United States Patent
Giordano et al.

(10) Patent No.: US 7,954,682 B2
(45) Date of Patent: Jun. 7, 2011

(54) SURGICAL INSTRUMENT WITH ELEMENTS TO COMMUNICATE BETWEEN CONTROL UNIT AND END EFFECTOR

(75) Inventors: James R. Giordano, Milford, OH (US); Frederick E. Shelton, IV, New Vienna, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 665 days.

(21) Appl. No.: 11/651,806

(22) Filed: Jan. 10, 2007

(65) Prior Publication Data
US 2008/0167671 A1 Jul. 10, 2008

(51) Int. Cl.
*A61B 17/32* (2006.01)
(52) U.S. Cl. ............... 227/175.1; 227/180.1; 227/181.1; 227/2; 227/19
(58) Field of Classification Search ............... 227/175.1, 227/180.1, 181.1, 2, 19
See application file for complete search history.

(56) References Cited

U.S. PATENT DOCUMENTS

| | | |
|---|---|---|
| 3,490,675 A | 1/1970 | Green et al. |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,629,107 A | 12/1986 | Fedotov et al. |

(Continued)

FOREIGN PATENT DOCUMENTS

CA 2458946 A1 3/2003

(Continued)

OTHER PUBLICATIONS

European Examination Report, Application No. 08250100.8, dated Feb. 19, 2009 (5 pages).

(Continued)

*Primary Examiner* — Rinaldi I. Rada
*Assistant Examiner* — Michelle Lopez

(57) ABSTRACT

A surgical instrument, such as an endoscopic or laparoscopic instrument, includes a shaft having a proximal end and a distal end. The shaft includes a first sensor element. An end effector is coupled to the distal end of the shaft. The end effector includes a second sensor element. A handle is connected to the proximate end of the shaft. The handle includes a control unit. The control unit is in communication with the first sensor element and the first sensor element is in wireless communication with the second sensor element.

22 Claims, 15 Drawing Sheets

U.S. PATENT DOCUMENTS

| | | |
|---|---|---|
| 4,641,076 A | 2/1987 | Linden |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,869,414 A | 9/1989 | Green et al. |
| 4,869,415 A | 9/1989 | Fox |
| 4,941,623 A | 7/1990 | Pruitt |
| 4,944,443 A | 7/1990 | Oddsen et al. |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,211,649 A | 5/1993 | Kohler et al. |
| 5,221,036 A | 6/1993 | Takase |
| 5,222,975 A | 6/1993 | Crainich |
| 5,236,440 A | 8/1993 | Hlavacek |
| 5,258,009 A | 11/1993 | Conners |
| 5,282,806 A | 2/1994 | Haber et al. |
| 5,282,829 A | 2/1994 | Hermes |
| 5,304,204 A | 4/1994 | Bregen |
| 5,342,395 A | 8/1994 | Jarrett et al. |
| 5,342,396 A | 8/1994 | Cook |
| 5,350,400 A | 9/1994 | Esposito et al. |
| 5,356,006 A | 10/1994 | Alpern et al. |
| 5,366,479 A | 11/1994 | McGarry et al. |
| 5,383,880 A | 1/1995 | Hooven |
| 5,395,033 A | 3/1995 | Byrne et al. |
| 5,397,324 A | 3/1995 | Carroll et al. |
| 5,405,072 A | 4/1995 | Zlock et al. |
| 5,413,272 A | 5/1995 | Green et al. |
| 5,417,361 A | 5/1995 | Williamson, IV |
| 5,425,745 A | 6/1995 | Green et al. |
| 5,433,721 A | 7/1995 | Hooven et al. |
| 5,465,895 A | 11/1995 | Knodel et al. |
| 5,474,566 A | 12/1995 | Alesi et al. |
| 5,478,354 A | 12/1995 | Tovey et al. |
| 5,480,089 A | 1/1996 | Blewett |
| 5,484,095 A | 1/1996 | Green et al. |
| 5,484,451 A | 1/1996 | Akopov et al. |
| 5,485,947 A | 1/1996 | Olson et al. |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,505,363 A | 4/1996 | Green et al. |
| 5,509,596 A | 4/1996 | Green et al. |
| 5,518,163 A | 5/1996 | Hooven |
| 5,518,164 A | 5/1996 | Hooven |
| 5,529,235 A | 6/1996 | Boiarski et al. |
| 5,535,934 A | 7/1996 | Boiarski et al. |
| 5,535,937 A | 7/1996 | Boiarski et al. |
| 5,543,119 A | 8/1996 | Sutter et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,579,978 A | 12/1996 | Green et al. |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,605,273 A | 2/1997 | Hamblin et al. |
| 5,607,094 A | 3/1997 | Clark et al. |
| 5,609,285 A | 3/1997 | Grant et al. |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,655,698 A | 8/1997 | Yoon |
| 5,657,921 A | 8/1997 | Young et al. |
| 5,658,300 A * | 8/1997 | Bito et al. ............ 606/143 |
| 5,662,258 A | 9/1997 | Knodel et al. |
| 5,662,260 A | 9/1997 | Yoon |
| 5,667,517 A | 9/1997 | Hooven |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,697,543 A | 12/1997 | Burdorff |
| 5,702,408 A | 12/1997 | Wales et al. |
| 5,704,087 A | 1/1998 | Strub |
| 5,704,534 A | 1/1998 | Huitema et al. |
| 5,706,998 A | 1/1998 | Plyley et al. |
| 5,709,334 A | 1/1998 | Sorrentino et al. |
| 5,709,680 A | 1/1998 | Yates et al. |
| 5,711,472 A | 1/1998 | Bryan |
| 5,713,505 A | 2/1998 | Huitema |
| 5,715,987 A | 2/1998 | Kelley et al. |
| 5,716,366 A | 2/1998 | Yates |
| 5,718,360 A | 2/1998 | Green et al. |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,807,393 A | 9/1998 | Williamson, IV et al. |
| 5,817,093 A | 10/1998 | Williamson, IV et al. |
| 5,820,009 A | 10/1998 | Melling et al. |
| 5,826,776 A | 10/1998 | Schulze et al. |
| 5,833,695 A | 11/1998 | Yoon |
| 5,836,503 A | 11/1998 | Ehrenfels et al. |
| 5,839,639 A | 11/1998 | Sauer et al. |

| | | | |
|---|---|---|---|
| 5,855,311 A | 1/1999 | Hamblin et al. | |
| 5,865,361 A | 2/1999 | Milliman et al. | |
| 5,868,760 A | 2/1999 | McGuckin, Jr. | |
| 5,876,401 A | 3/1999 | Schulze et al. | |
| 5,893,506 A | 4/1999 | Powell | |
| 5,897,562 A | 4/1999 | Bolanos et al. | |
| 5,901,895 A | 5/1999 | Heaton et al. | |
| 5,908,427 A | 6/1999 | McKean et al. | |
| 5,911,353 A | 6/1999 | Bolanos et al. | |
| 5,915,616 A | 6/1999 | Viola et al. | |
| 5,918,791 A | 7/1999 | Sorrentino et al. | |
| 5,919,198 A | 7/1999 | Graves, Jr. et al. | |
| 5,941,442 A | 8/1999 | Geiste et al. | |
| 5,954,259 A | 9/1999 | Viola et al. | |
| 6,010,054 A | 1/2000 | Johnson et al. | |
| 6,024,741 A | 2/2000 | Williamson, IV et al. | |
| 6,032,849 A | 3/2000 | Mastri et al. | |
| 6,045,560 A | 4/2000 | McKean et al. | |
| 6,083,242 A | 7/2000 | Cook | |
| 6,086,600 A | 7/2000 | Kortenbach | |
| 6,099,551 A | 8/2000 | Gabbay | |
| 6,102,271 A | 8/2000 | Longo et al. | |
| 6,119,913 A | 9/2000 | Adams et al. | |
| 6,126,058 A | 10/2000 | Adams et al. | |
| 6,171,330 B1 | 1/2001 | Benchetrit | |
| 6,181,105 B1 | 1/2001 | Cutolo et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,273,897 B1 | 8/2001 | Dalessandro et al. | |
| 6,302,311 B1 | 10/2001 | Adams et al. | |
| 6,315,184 B1 | 11/2001 | Whitman | |
| 6,330,965 B1 | 12/2001 | Milliman et al. | |
| 6,346,077 B1 | 2/2002 | Taylor et al. | |
| 6,387,113 B1 | 5/2002 | Hawkins et al. | |
| RE37,814 E | 8/2002 | Allgeyer | |
| 6,436,107 B1 | 8/2002 | Wang et al. | |
| 6,443,973 B1 | 9/2002 | Whitman | |
| 6,488,196 B1 | 12/2002 | Fenton, Jr. | |
| 6,488,197 B1 | 12/2002 | Whitman | |
| 6,491,201 B1 | 12/2002 | Whitman | |
| 6,505,768 B2 | 1/2003 | Whitman | |
| 6,517,565 B1 | 2/2003 | Whitman et al. | |
| 6,578,751 B2 | 6/2003 | Hartwick | |
| 6,588,643 B2 | 7/2003 | Bolduc et al. | |
| 6,596,432 B2 | 7/2003 | Kawakami et al. | |
| 6,601,749 B2 | 8/2003 | Sullivan et al. | |
| 6,616,686 B2 | 9/2003 | Coleman et al. | |
| 6,619,529 B2 | 9/2003 | Green et al. | |
| 6,629,630 B2 | 10/2003 | Adams | |
| 6,629,988 B2 | 10/2003 | Weadock | |
| 6,644,532 B2 | 11/2003 | Green et al. | |
| 6,648,816 B2 | 11/2003 | Irion et al. | |
| 6,666,875 B1 | 12/2003 | Sakurai et al. | |
| 6,679,410 B2 | 1/2004 | Würsch et al. | |
| 6,681,978 B2 | 1/2004 | Geiste et al. | |
| 6,681,979 B2 | 1/2004 | Whitman | |
| 6,695,199 B2 | 2/2004 | Whitman | |
| 6,698,643 B2 | 3/2004 | Whitman | |
| 6,716,233 B1 * | 4/2004 | Whitman | 606/219 |
| 6,755,338 B2 | 6/2004 | Hahnen et al. | |
| 6,769,594 B2 | 8/2004 | Orban, III | |
| 6,773,438 B1 | 8/2004 | Knodel et al. | |
| 6,793,652 B1 | 9/2004 | Whitman et al. | |
| 6,805,273 B2 | 10/2004 | Bilotti et al. | |
| 6,817,508 B1 | 11/2004 | Racenet et al. | |
| 6,817,509 B2 | 11/2004 | Geiste et al. | |
| 6,830,174 B2 | 12/2004 | Hillstead et al. | |
| 6,843,403 B2 | 1/2005 | Whitman | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| RE38,708 E | 3/2005 | Bolanos et al. | |
| 6,874,669 B2 | 4/2005 | Adams et al. | |
| 6,877,647 B2 | 4/2005 | Green et al. | |
| 6,905,057 B2 | 6/2005 | Swayze et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 6,988,650 B2 | 1/2006 | Schwemberger et al. | |
| 7,000,818 B2 | 2/2006 | Shelton, IV et al. | |
| 7,000,819 B2 | 2/2006 | Swayze et al. | |
| 7,008,435 B2 | 3/2006 | Cummins | |
| 7,025,743 B2 | 4/2006 | Mann et al. | |
| 7,032,798 B2 * | 4/2006 | Whitman et al. | 227/175.1 |
| 7,032,799 B2 | 4/2006 | Viola et al. | |
| 7,044,352 B2 | 5/2006 | Shelton, IV et al. | |
| 7,044,353 B2 | 5/2006 | Mastri et al. | |
| 7,055,731 B2 | 6/2006 | Shelton, IV et al. | |
| 7,056,330 B2 | 6/2006 | Gayton | |
| 7,070,083 B2 | 7/2006 | Jankowski | |
| 7,077,856 B2 | 7/2006 | Whitman | |
| 7,080,769 B2 | 7/2006 | Vresh et al. | |
| 7,083,075 B2 | 8/2006 | Swayze et al. | |
| 7,083,571 B2 * | 8/2006 | Wang et al. | 600/102 |
| 7,090,684 B2 | 8/2006 | McGuckin, Jr. et al. | |
| 7,108,695 B2 | 9/2006 | Witt et al. | |
| 7,108,709 B2 | 9/2006 | Cummins | |
| 7,111,769 B2 | 9/2006 | Wales et al. | |
| 7,114,642 B2 | 10/2006 | Whitman | |
| 7,118,582 B1 | 10/2006 | Wang et al. | |
| 7,121,446 B2 | 10/2006 | Arad et al. | |
| 7,128,253 B2 | 10/2006 | Mastri et al. | |
| 7,128,254 B2 | 10/2006 | Shelton, IV et al. | |
| 7,140,527 B2 | 11/2006 | Ehrenfels et al. | |
| 7,147,138 B2 | 12/2006 | Shelton, IV | |
| 7,159,750 B2 | 1/2007 | Racenet et al. | |
| 7,168,604 B2 | 1/2007 | Milliman et al. | |
| 7,188,758 B2 | 3/2007 | Viola et al. | |
| 7,207,471 B2 | 4/2007 | Heinrich et al. | |
| 7,207,472 B2 | 4/2007 | Wukusick et al. | |
| 7,210,609 B2 | 5/2007 | Leiboff et | |
| 7,213,736 B2 | 5/2007 | Wales et al. | |
| 7,220,272 B2 | 5/2007 | Weadock | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,246,734 B2 | 7/2007 | Shelton, IV | |
| 7,258,262 B2 | 8/2007 | Mastri et al. | |
| 7,260,431 B2 * | 8/2007 | Libbus et al. | 607/4 |
| 7,278,562 B2 | 10/2007 | Mastri et al. | |
| 7,278,563 B1 | 10/2007 | Green | |
| 7,296,724 B2 | 11/2007 | Green et al. | |
| 7,303,106 B2 | 12/2007 | Milliman et al. | |
| 7,303,107 B2 | 12/2007 | Milliman et al. | |
| 7,303,108 B2 | 12/2007 | Shelton, IV | |
| 7,303,556 B2 | 12/2007 | Metzger | |
| 7,328,828 B2 | 2/2008 | Ortiz et al. | |
| 7,328,829 B2 | 2/2008 | Arad et al. | |
| 7,354,447 B2 | 4/2008 | Shelton, IV et al. | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,398,907 B2 | 7/2008 | Racenet et al. | |
| 7,398,908 B2 | 7/2008 | Holsten et al. | |
| 7,404,508 B2 | 7/2008 | Smith et al. | |
| 7,404,509 B2 | 7/2008 | Ortiz et al. | |
| 7,407,075 B2 | 8/2008 | Holsten et al. | |
| 7,407,078 B2 | 8/2008 | Shelton, IV et al. | |
| 7,410,086 B2 | 8/2008 | Ortiz et al. | |
| 7,416,101 B2 | 8/2008 | Shelton, IV et al. | |
| 7,422,136 B1 | 9/2008 | Marczyk | |
| 7,422,139 B2 | 9/2008 | Shelton, IV et al. | |
| 7,424,965 B2 | 9/2008 | Racenet et al. | |
| 7,431,188 B1 | 10/2008 | Marczyk | |
| 7,431,189 B2 | 10/2008 | Shelton, IV et al. | |
| 7,431,730 B2 | 10/2008 | Viola | |

| | | |
|---|---|---|
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,847 B2 * | 12/2008 | Viola et al. ............... 227/175.2 |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,559,450 B2 | 7/2009 | Wales et al. |
| 7,631,793 B2 | 12/2009 | Rethy et al. |
| 7,665,646 B2 | 2/2010 | Prommersberger |
| 7,699,204 B2 | 4/2010 | Viola |
| 7,780,054 B2 | 8/2010 | Wales |
| 2002/0117534 A1 | 8/2002 | Green et al. |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0108357 A1 | 6/2004 | Milliman et al. |
| 2004/0116952 A1 | 6/2004 | Sakurai et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0254608 A1 | 12/2004 | Huitema et al. |
| 2005/0032511 A1 | 2/2005 | Malone et al. |
| 2005/0059997 A1 | 3/2005 | Bauman et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0131390 A1 | 6/2005 | Heinrich et al. |
| 2005/0143759 A1 | 6/2005 | Kelly |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0025812 A1 | 2/2006 | Shelton, IV |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0151567 A1 | 7/2006 | Roy |
| 2006/0180634 A1 | 8/2006 | Shelton, IV et al. |
| 2006/0212069 A1 | 9/2006 | Shelton, IV |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0034668 A1 | 2/2007 | Holsten et al. |
| 2007/0045379 A1 | 3/2007 | Shelton, IV |
| 2007/0073341 A1 | 3/2007 | Smith et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0246505 A1 | 10/2007 | Pace-Floridia et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167672 A1 | 7/2008 | Giordano et al. |
| 2008/0167736 A1 | 7/2008 | Swayze et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton et al. |
| 2008/0308606 A1 | 12/2008 | Timm et al. |
| 2008/0308607 A1 | 12/2008 | Timm et al. |

| | | |
|---|---|---|
| 2008/0308608 A1 | 12/2008 | Prommersberger |
| 2008/0314954 A1 | 12/2008 | Boudreaux |
| 2008/0314955 A1 | 12/2008 | Boudreaux et al. |
| 2008/0314956 A1 | 12/2008 | Boudreaux |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0157067 A1 | 6/2009 | Kane et al. |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255978 A1 | 10/2009 | Viola et al. |
| 2009/0289096 A1 | 11/2009 | Shelton, IV et al. |
| 2009/0292283 A1 | 11/2009 | Odom |
| 2010/0032470 A1 | 2/2010 | Hess et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0213241 A1 | 8/2010 | Bedi |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 1775926 A | 1/1972 |
| DE | 3210466 A1 | 9/1983 |
| DE | 9412228 U | 9/1994 |
| DE | 19924311 A1 | 11/2000 |
| DE | 69328576 T2 | 1/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0070230 B1 | 10/1985 |
| EP | 0033548 B1 | 5/1986 |
| EP | 0276104 A2 | 7/1988 |
| EP | 0639349 A2 | 2/1994 |
| EP | 0324636 B1 | 3/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |
| EP | 0770355 A1 | 5/1997 |
| EP | 0503662 B1 | 6/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0676173 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0741996 B1 | 2/2004 |
| EP | 0705570 B1 | 4/2004 |
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520521 A1 | 4/2005 |
| EP | 1520523 A1 | 4/2005 |
| EP | 1520525 A1 | 4/2005 |

| | | | | | | |
|---|---|---|---|---|---|---|
| EP | 1522264 | A1 | 4/2005 | WO | WO 97/39688 A2 | 10/1997 |
| EP | 1523942 | A2 | 4/2005 | WO | WO 98/17180 A1 | 4/1998 |
| EP | 1550408 | A1 | 7/2005 | WO | WO 98/30153 A1 | 7/1998 |
| EP | 1557129 | A1 | 7/2005 | WO | WO 99/12483 A1 | 3/1999 |
| EP | 1064883 | B1 | 8/2005 | WO | WO 99/15086 A1 | 4/1999 |
| EP | 1157666 | B1 | 9/2005 | WO | WO 99/34744 A1 | 7/1999 |
| EP | 1621138 | A2 | 2/2006 | WO | WO 99/45849 A1 | 9/1999 |
| EP | 1621139 | A2 | 2/2006 | WO | WO 00/24322 A1 | 5/2000 |
| EP | 1621141 | A2 | 2/2006 | WO | WO 00/57796 A1 | 10/2000 |
| EP | 1621145 | A2 | 2/2006 | WO | WO 00/64365 A1 | 11/2000 |
| EP | 1621151 | A2 | 2/2006 | WO | WO 00/72762 A1 | 12/2000 |
| EP | 1652481 | A2 | 5/2006 | WO | WO 00/72765 A1 | 12/2000 |
| EP | 1382303 | B1 | 6/2006 | WO | WO 01/05702 A1 | 1/2001 |
| EP | 1045672 | B1 | 8/2006 | WO | WO 01/10482 A1 | 2/2001 |
| EP | 1617768 | B1 | 8/2006 | WO | WO 01/54594 A1 | 8/2001 |
| EP | 1702567 | A2 | 9/2006 | WO | WO 01/62158 A1 | 8/2001 |
| EP | 1129665 | B1 | 11/2006 | WO | WO 01/62162 A1 | 8/2001 |
| EP | 1400206 | B1 | 11/2006 | WO | WO 01/62164 A2 | 8/2001 |
| EP | 1256317 | B1 | 12/2006 | WO | WO 01/91646 A1 | 12/2001 |
| EP | 1728473 | A1 | 12/2006 | WO | WO 02/07608 A2 | 1/2002 |
| EP | 1728475 | A2 | 12/2006 | WO | WO 02/07618 A1 | 1/2002 |
| EP | 1479346 | B1 | 1/2007 | WO | WO 02/17799 A1 | 3/2002 |
| EP | 1484024 | B1 | 1/2007 | WO | WO 02/19920 A1 | 3/2002 |
| EP | 1754445 | A2 | 2/2007 | WO | WO 02/30297 A2 | 4/2002 |
| EP | 1759812 | A1 | 3/2007 | WO | WO 02/32322 A1 | 4/2002 |
| EP | 1769756 | A1 | 4/2007 | WO | WO 02/43571 A2 | 6/2002 |
| EP | 1769758 | A1 | 4/2007 | WO | WO 02/058568 A1 | 8/2002 |
| EP | 1785097 | A2 | 5/2007 | WO | WO 02/060328 A1 | 8/2002 |
| EP | 1790293 | A2 | 5/2007 | WO | WO 02/067785 A2 | 9/2002 |
| EP | 1800610 | A1 | 6/2007 | WO | WO 02/098302 A1 | 12/2002 |
| EP | 1300117 | B1 | 8/2007 | WO | WO 03/000138 A2 | 1/2003 |
| EP | 1813199 | A1 | 8/2007 | WO | WO 03/001329 A2 | 1/2003 |
| EP | 1813201 | A1 | 8/2007 | WO | WO 03/013363 A1 | 2/2003 |
| EP | 1813203 | A2 | 8/2007 | WO | WO 03/020106 A2 | 3/2003 |
| EP | 1813207 | A1 | 8/2007 | WO | WO 03/020139 A2 | 3/2003 |
| EP | 1813209 | A1 | 8/2007 | WO | WO 03/079909 A3 | 3/2003 |
| EP | 1402821 | B1 | 12/2007 | WO | WO 03/030743 A2 | 4/2003 |
| EP | 1872727 | A1 | 1/2008 | WO | WO 03/037193 | 5/2003 |
| EP | 1839596 | A2 | 2/2008 | WO | WO 03/047436 A3 | 6/2003 |
| EP | 1897502 | A1 | 3/2008 | WO | WO 03/057048 A1 | 7/2003 |
| EP | 1702568 | B1 | 7/2008 | WO | WO 03/057058 A1 | 7/2003 |
| EP | 1970014 | A1 | 9/2008 | WO | WO 03/063694 A1 | 8/2003 |
| EP | 1980213 | A2 | 10/2008 | WO | WO 03/077769 A1 | 9/2003 |
| EP | 1759645 | B1 | 11/2008 | WO | WO 03/082126 A1 | 10/2003 |
| EP | 1693008 | B1 | 12/2008 | WO | WO 03/088845 A2 | 10/2003 |
| EP | 1759640 | B1 | 12/2008 | WO | WO 03/090630 A2 | 11/2003 |
| EP | 2000102 | A2 | 12/2008 | WO | WO 03/094743 A1 | 11/2003 |
| EP | 1749486 | B1 | 3/2009 | WO | WO 03/094745 A1 | 11/2003 |
| EP | 2090256 | A2 | 8/2009 | WO | WO 03/094746 A1 | 11/2003 |
| EP | 1813206 | B1 | 4/2010 | WO | WO 03/094747 A1 | 11/2003 |
| EP | 1769754 | B1 | 6/2010 | WO | WO 03090630 A2 * | 11/2003 |
| EP | 1702570 | B1 | 10/2010 | WO | WO 03/101313 A1 | 12/2003 |
| FR | 999646 | A | 2/1952 | WO | WO 03/105698 A2 | 12/2003 |
| FR | 1112936 | A | 3/1956 | WO | WO 03/105702 A2 | 12/2003 |
| FR | 2765794 | A | 1/1999 | WO | WO 2004/006980 A2 | 1/2004 |
| GB | 939929 | A | 10/1963 | WO | WO 2004/028585 A2 | 4/2004 |
| GB | 1210522 | A | 10/1970 | WO | WO 2004/032754 A2 | 4/2004 |
| GB | 2336214 | A | 10/1999 | WO | WO 2004/032760 A2 | 4/2004 |
| JP | 6007357 | A | 1/1994 | WO | WO 2004/032762 A1 | 4/2004 |
| JP | 7051273 | A | 2/1995 | WO | WO 2004/032763 A2 | 4/2004 |
| JP | 8033641 | A | 2/1996 | WO | WO 2004/047653 A2 | 6/2004 |
| JP | 8229050 | A | 9/1996 | WO | WO 2004/049956 A2 | 6/2004 |
| JP | 2000287987 | A | 10/2000 | WO | WO 2004/086987 A1 | 10/2004 |
| JP | 2001286477 | A | 10/2001 | WO | WO 2004/096057 A2 | 11/2004 |
| JP | 2002369820 | A | 12/2002 | WO | WO 2004/105621 A1 | 12/2004 |
| JP | 2005505322 | T | 2/2005 | WO | WO 2004/112618 A2 | 12/2004 |
| JP | 2005103293 | A | 4/2005 | WO | WO 2004/112652 A2 | 12/2004 |
| RU | 2187249 | C2 | 8/2002 | WO | WO 2005/027983 A2 | 3/2005 |
| RU | 2225170 | C2 | 3/2004 | WO | WO 2005/037329 A2 | 4/2005 |
| SU | 1377053 | A1 | 2/1988 | WO | WO 2005/078892 A1 | 8/2005 |
| SU | 1561964 | A1 | 5/1990 | WO | WO 2005/096954 A2 | 10/2005 |
| SU | 1722476 | A1 | 3/1992 | WO | WO 2005/112808 A1 | 12/2005 |
| WO | WO 93/08755 | A1 | 5/1993 | WO | WO 2005/115251 A2 | 12/2005 |
| WO | WO 95/18572 | A1 | 7/1995 | WO | WO 2006/044490 A2 | 4/2006 |
| WO | WO 95/23557 | A1 | 9/1995 | WO | WO 2006/044581 A2 | 4/2006 |
| WO | WO 95/29639 | A1 | 11/1995 | WO | WO 2006/044810 A2 | 4/2006 |
| WO | WO 96/22055 | A1 | 7/1996 | WO | WO 2006/083748 A1 | 8/2006 |
| WO | WO 96/35464 | A1 | 11/1996 | WO | WO 2006/115958 A1 | 11/2006 |
| WO | WO 97/34533 | A1 | 9/1997 | WO | WO 2006/132992 A1 | 12/2006 |

| | | | |
|---|---|---|---|
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |
| WO | WO 2008/109125 A1 | 9/2008 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

* cited by examiner

SURGICAL INSTRUMENT WITH ELEMENTS TO COMMUNICATE BETWEEN CONTROL UNIT AND END EFFECTOR

CROSS REFERENCE TO RELATED APPLICATION

The present application is related to the following, concurrently-filed U.S. patent applications, which are incorporated herein by reference:

(1) U.S. patent application Ser. No. 11/651,715, now U.S. Patent Publication No. 2008/0167522, entitled "SURGICAL INSTRUMENT WITH WIRELESS COMMUNICATION BETWEEN CONTROL UNIT AND SENSOR TRANSPONDERS," by J. Giordano et al.;

(2) U.S. patent application Ser. No. 11/651,807, now U.S. Patent Publication No. 2008/0167672,entitled "SURGICAL INSTRUMENT WITH WIRELESS COMMUNICATION BETWEEN CONTROL UNIT AND REMOTE SENSOR," by J. Giordano et al.;

(3) U.S. patent application Ser. No. 11/651,768, now U.S. Pat. No. 7,721,931, entitled "PREVENTION OF CARTRIDGE REUSE IN A SURGICAL INSTRUMENT," by F. Shelton et al.;

(4) U.S. patent application Ser. No. 11/651,771, now U.S. Pat. No. 7,738,971, entitled "POST-STERILIZATION PROGRAMMING OF SURGICAL INSTRUMENTS," by J. Swayze et al.;

(5) U.S. patent application Ser. No. 11/651,788, now U.S. Pat. No. 7,721,936, entitled "INTERLOCK AND SURGICAL INSTRUMENT INCLUDING SAME," by F. Shelton et al.; and (6) U.S. patent application Ser. No. 11/651,785, now U.S. Patent Publication No. 2008/0167644, entitled "SURGICAL INSTRUMENT WITH ENHANCED BATTERY PERFORMANCE," by F. Shelton et al.;

BACKGROUND

Endoscopic surgical instruments are often preferred over traditional open surgical devices because a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which discloses an endocutter with distinct closing and firing actions. A clinician using this device is able to close the jaw members upon tissue to position the tissue prior to firing. Once the clinician has determined that the jaw members are properly gripping tissue, the clinician can then fire the surgical stapler with a single firing stroke, thereby severing and stapling the tissue. The simultaneous severing and stapling avoids complications that may arise when performing such actions sequentially with different surgical tools that respectively only sever and staple.

One specific advantage of being able to close upon tissue before firing is that the clinician is able to verify via an endoscope that the desired location for the cut has been achieved, including that a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Endoscopic staplers/cutters continue to increase in complexity and function with each generation. One of the main reasons for this is the quest to lower force-to-fire (FTF) to a level that all or a great majority of surgeons can handle. One known solution to lower FTF it use $CO_2$ or electrical motors. These devices have not faired much better than traditional hand-powered devices, but for a different reason. Surgeons typically prefer to experience proportionate force distribution to that being experienced by the end effector in the forming of the staple to assure them that the cutting/stapling cycle is complete, with the upper limit within the capabilities of most surgeons (usually around 15-30 lbs). They also typically want to maintain control of deploying the staples and being able to stop at anytime if the forces felt in the handle of the device feel too great or for some other clinical reason.

To address this need, so-called "power-assist" endoscopic surgical instruments have been developed in which a supplemental power source aids in the firing of the instrument. For example, in some power-assist devices, a motor provides supplemental electrical power to the power input by the user from squeezing the firing trigger. Such devices are capable of providing loading force feedback and control to the operator to reduce the firing force required to be exerted by the operator in order to complete the cutting operation. One such power-assist device is described in U.S. patent application Ser. No. 11/343,573, filed Jan. 31, 2006 by Shelton et al., entitled "MOTOR-DRIVEN SURGICAL CUTTING AND FASTENING INSTRUMENT WITH LOADING FORCE FEEDBACK," ("the '573 application") which is incorporated herein by reference.

These power-assist devices often include other components that purely mechanical endoscopic surgical instruments do not, such as sensors and control systems. One challenge in using such electronics in a surgical instrument is delivering power and/or information or data to and from the sensors, particularly when there is a free rotating joint or an articulation pivot in the surgical instrument. Sensors may be employed to determine the status of the staple cartridge, user input loads, internal instrument loadings, stapler progress during closure and firing, and many other aspects. Accordingly, there may be a need for determining the status of the staple cartridge through the use of one or more passive and/or active sensor elements that do not require power and/or a wired electrical connection.

SUMMARY

In one general aspect, the present invention is directed to a surgical instrument, such as an endoscopic or laparoscopic instrument. According to one embodiment, the surgical instrument includes a shaft having a proximal end and a distal end. The shaft includes a first sensor element. An end effector is coupled to the distal end of the shaft. The end effector includes a second sensor element. A handle is connected to the proximate end of the shaft. The handle includes a control unit. The control unit is in communication with the first sensor element and the first sensor element is in wireless communication with the second sensor element.

FIGURES

Various embodiments of the present invention are described herein by way of example in conjunction with the following figures wherein.

DETAILED DESCRIPTION

Figure 1:
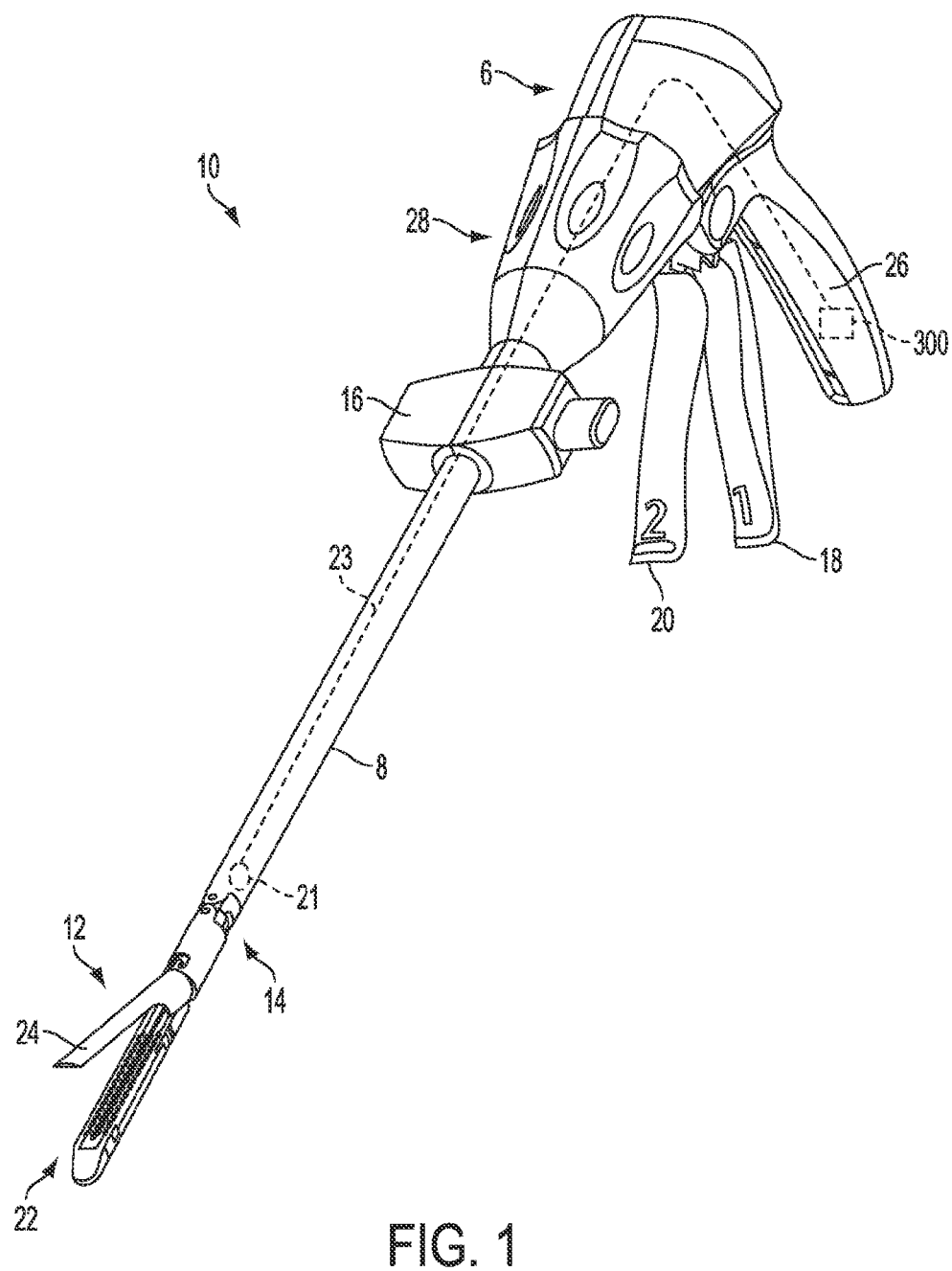
FIGS. 1 and 2 are perspective views of a surgical instrument according to various embodiments of the present invention.

In one embodiment, the present invention is directed to a surgical instrument, such as an endoscopic or laparoscopic instrument. The surgical instrument may comprise a shaft having a distal end connected to an end effector and a handle connected to a proximate end of the shaft. The handle may comprise a control unit (e.g., a microcontroller) that is in communication with a first sensor element. Further, the surgical instrument may comprise a rotational joint for rotating the shaft. In such a case, the surgical instrument may comprise the first element located in the shaft distally from the rotational joint. The first element may be coupled to the control unit either by a wired or wireless electrical connection. A second element may be located in the end effector and may be coupled to the first element by a wireless electrical connection. The first and second elements may be connected and/or coupled by a wired or a wireless electrical connection.

The control unit may communicate with the second sensor element in the end effector without a direct wired electrical connection through complex mechanical joints like a rotating joint or articulating pivot where it may be difficult to maintain such a wired electrical connection. In addition, because the distances between the inductive elements may be fixed and known, the couplings between the first and second sensor elements may be optimized for inductive and/or electromagnetic transfer of energy. Also, the distances may be relatively short so that relatively low power signals may be used to minimize interference with other systems in the use environment of the instrument.

In another embodiment of the present invention, the electrically conductive shaft of the surgical instrument may serve as an antenna for the control unit to wirelessly communicate signals to and from one or more sensor elements. For example, one or more sensor elements may be located on or disposed in a nonconductive component of the end effector, such as a plastic cartridge, thereby insulating the sensor element from conductive components of the end effector and the shaft. In addition, the control unit in the handle may be electrically coupled to the shaft. In that way, the shaft and/or the end effector may serve as an antenna for the control unit to radiate signals from the control unit to the one or more sensor elements and/or receive radiated echo response signals from the one or more sensor elements. Such a design is particularly useful in surgical instruments having complex mechanical joints (such as rotary joints) and articulating pivots, which make it difficult to use a direct wired electrical connection between the sensor elements and the control unit for communicating electrical signals therebetween.

Various embodiments of the present invention are directed generally to a surgical instrument comprising one or more sensor elements to sense the location, type, presence and/or status of various components of interest disposed on the surgical instrument. In one embodiment, the present invention is directed generally to a surgical instrument having one or more sensor elements to sense the location, type, presence and/or status of various components of interest disposed in an end effector portion of the surgical instrument. These components of interest may comprise, for example, a sled, a staple cartridge, a cutting instrument or any other component that may be disposed on the surgical instrument and more particularly disposed in the end effector portion thereof. Although the present invention may be used with any type of surgical instrument such as endoscopic or laparoscopic surgical instruments, it is particularly useful for surgical instruments comprising one or more free rotating joints or an articulation pivots that make it difficult to use wired electrical connections to the one or more passive and/or active sensor elements.

The one or more sensor elements may be passive or active sensor elements adapted to communicate with a control unit in any suitable manner. In various embodiments, some of the sensor elements may not be supplied power over a wired electrical connection and as described herein, neither the passive nor the active sensor elements may comprise an internal power supply. The sensor elements may operate using the power provided by the minute electrical current induced in the sensor element itself or an antenna coupled to the sensor element by an incoming radio frequency (RF) interrogation signal transmitted by the control unit. This means that the antenna and/or the sensor element itself may be designed to collect power from the incoming interrogation signal and also to transmit an outbound backscatter signal in response thereto. The lack of an onboard power supply means that the sensor elements may have a relatively small form factor. In embodiments comprising a passive sensor element RF interrogation signals may be received by the passive sensor element wirelessly over a predetermined channel. The incident electromagnetic radiation associated with the RF interrogation signals is then scattered or reflected back to the interrogating source such as the control unit. Thus, the passive sensor element signals by backscattering the carrier of the RF interrogation signal from the control unit. In embodiments comprising an active sensor element, on the other hand, just enough power may be received from the RF interrogation signals to cause the active sensor element to power up and transmit an analog or digital signal back to the control unit in response in response to the RF interrogation signal. The control unit may be referred to as a reader, interrogator or the like.

In one embodiment, the status of a component (e.g., sled, staple cartridge, cutting instrument) located in the end effector portion of the surgical instrument may be determined through the use of a system comprising passive and/or active sensor elements coupled to a control unit. The passive sensor elements may be formed of or comprise passive hardware elements such as resistive, inductive and/or capacitive elements or any combination thereof. The active sensor elements may be formed of or comprise active hardware elements. These active hardware elements may be integrated and/or discrete circuit elements or any combination thereof. Examples of integrated and/or discrete hardware elements are described herein below.

In one embodiment, the system may comprise a control unit coupled to a primary sensor element (primary element) disposed at a distal end of a shaft of the surgical instrument prior to an articulation pivot (as described below) and a secondary sensor element (secondary element) disposed on a component of interest in an end effector portion of the surgical instrument located subsequent to the articulation pivot (e.g., on a sled as described below). Rather than transmitting continuous power to the secondary element over a wired electrical connection, the primary element wirelessly interrogates or illuminates the secondary element by transmitting an electromagnetic pulse signal over a channel at a predetermined frequency, duration and repetition rate. When the interrogation pulse signal is incident upon, i.e., strikes or illuminates, the secondary element, it generated an echo response signal. The echo response signal is a reflection of the electromagnetic energy incident upon the secondary element. After transmitting the interrogation signal, the primary element listens for the echo response signal reflected from the secondary element and couples the echo response signal to the control unit in a suitable form for subsequent processing. The echo response signal may be of the same frequency as the interrogation pulse or some harmonic frequency thereof. The amount of reflected energy in the echo response signal depends upon the material, shape and size of the secondary element. The amount of reflected energy in the echo response signal also depends upon the distance between the primary element and the secondary element. Therefore, the material, shape and size of the secondary element as well as the relative distance between the primary and secondary elements may be selected to generate a unique echo response signal that is indicative of a desired measurement associated with the component of interest coupled to the secondary element. For example, unique echo response signals may indicate the location, type, presence and/or status of various components and sub-components disposed in the surgical instrument. Especially, the various components and sub-components disposed in the end effector portion of the surgical instrument subsequent to a freely rotating joint or articulation pivot that may make it difficult or impractical to provide a wired electrical connection between the primary and the secondary elements. The echo response signals also may be used to determine the distance between the primary and secondary elements. In this manner, the secondary element may be made integral with or may be attached to a component of interest and the echo response signal may provide information associated with the component of interest. This arrangement may eliminate the need to transmit or provide power to the secondary element over a wired connection and may be a cost effective solution to providing various additional passive and/or active sensor elements in the surgical instrument. Before describing aspects of the system, one type of surgical instrument in which embodiments of the present invention may be used—an endoscopic stapling and cutting instrument (i.e., an endocutter)—is first described by way of illustration.

Figure 2:
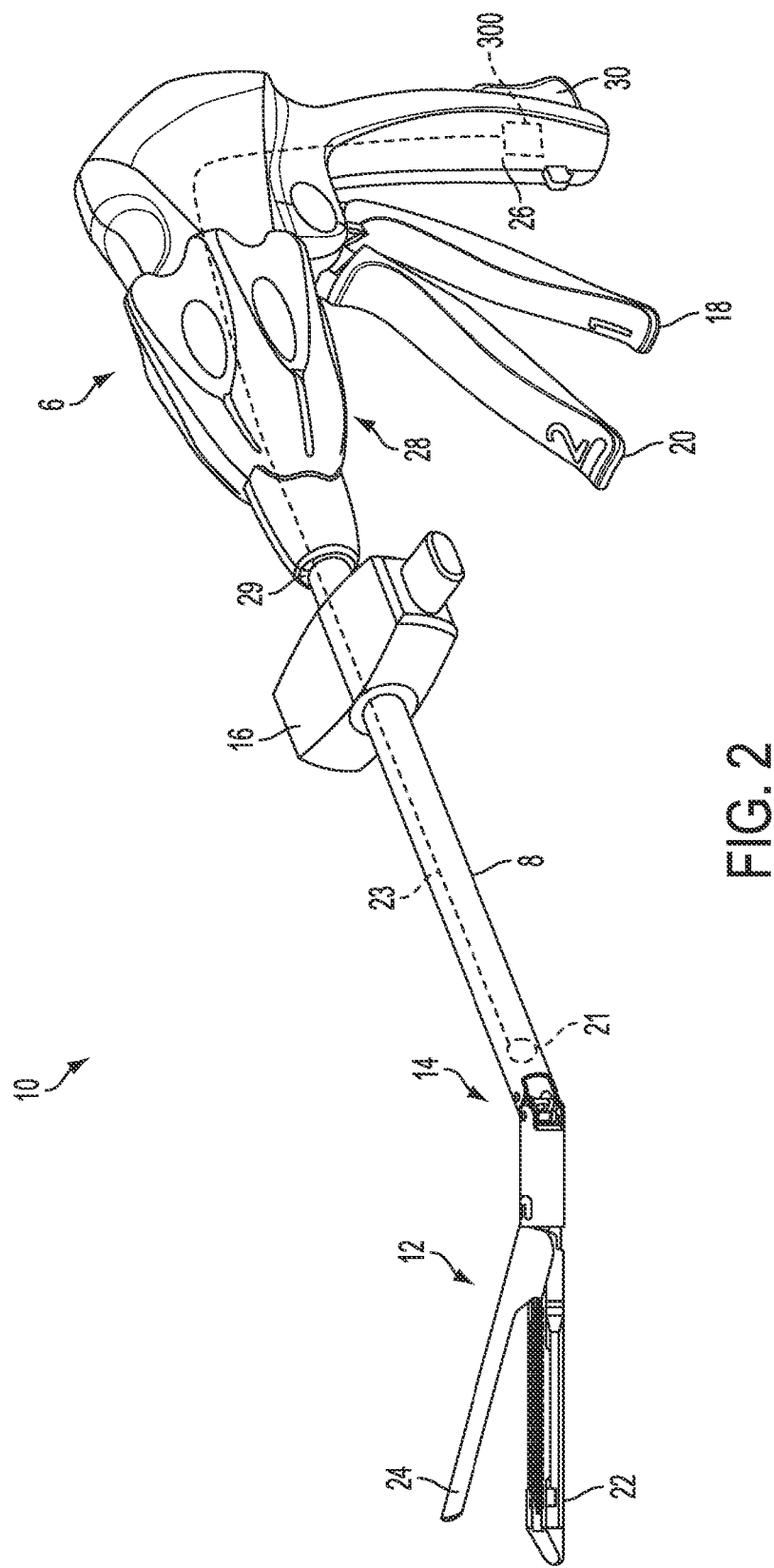

FIGS. 1 and 2 depict an endoscopic surgical instrument 10 that comprises a handle 6, a shaft 8, and an articulating end effector 12 pivotally connected to the shaft 8 at an articulation pivot 14. Correct placement and orientation of the end effector 12 may be facilitated by controls on the hand 6, including (1) a rotation knob 28 for rotating the closure tube (described in more detail below in connection with FIGS. 4-5) at a free rotating joint 29 of the shaft 8 to thereby rotate the end effector 12 and (2) an articulation control 16 to effect rotational articulation of the end effector 12 about the articulation pivot 14. In the illustrated embodiment, the end effector 12 is configured to act as an endocutter for clamping, severing and stapling tissue, although in other embodiments, different types of end effectors may be used, such as end effectors for other types of surgical instruments, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by the preferably elongate shaft 8. The handle may comprise a control unit 300 (described below) in communication with a first element 21 by way of an electrical connection 23. The electrical connection 23 may be a wired electrical connection such as an electrically conductive insulated wire or may be a wireless electrical connection. The electrically conductive insulated wire may be made of an electrically conductive polymer and/or metal (e.g., copper) and may be sufficiently flexible so that it could pass through the articulation control 16, the rotation knob 28, the free rotating joint 29 and other components in the handle 6 of the instrument 10 without being damaged by rotation. The first element 21 may be disposed at a distal end of the shaft 8 prior to the articulation pivot 14. A second element 35 (shown in FIG. 3 below) may be disposed in the articulating end effector 12 and is in wireless communication with the first element 21. The operation of the first and second elements 21, 23 and the control unit 300 is described below. In one embodiment, a clinician or operator of the instrument 10 may articulate the end effector 12 relative to the shaft 8 by utilizing the articulation control 16, as described in more detail in pending U.S. patent application Ser. No. 11/329,020, filed Jan. 10, 2006, entitled "SURGICAL INSTRUMENT HAVING AN ARTICULATING END EFFECTOR," by Geoffrey C. Hueil et al., which is incorporated herein by reference.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position, the firing trigger 20 may rotate slightly toward the pistol grip 26 so that it can be reached by the operator using one hand. Then the operator may pivotally draw the firing trigger 20 toward the pistol grip 12 to cause the stapling and severing of clamped tissue in the end effector 12. The '573 application describes various configurations for locking and unlocking the closure trigger 18. In other embodiments, different types of clamping members besides the anvil 24 could be used, such as, for example, an opposing jaw, etc.

It will be appreciated that the terms "proximal" and "distal" are used herein with reference to a clinician gripping the handle 6 of the instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. When the clinician removes pressure from the firing trigger 20, it returns to the open position (shown in FIGS. 1 and 2). A release button 30 on the handle 6, and in this example, on the pistol grip 26 of the handle, when depressed may release the locked closure trigger 18.

Figure 3:
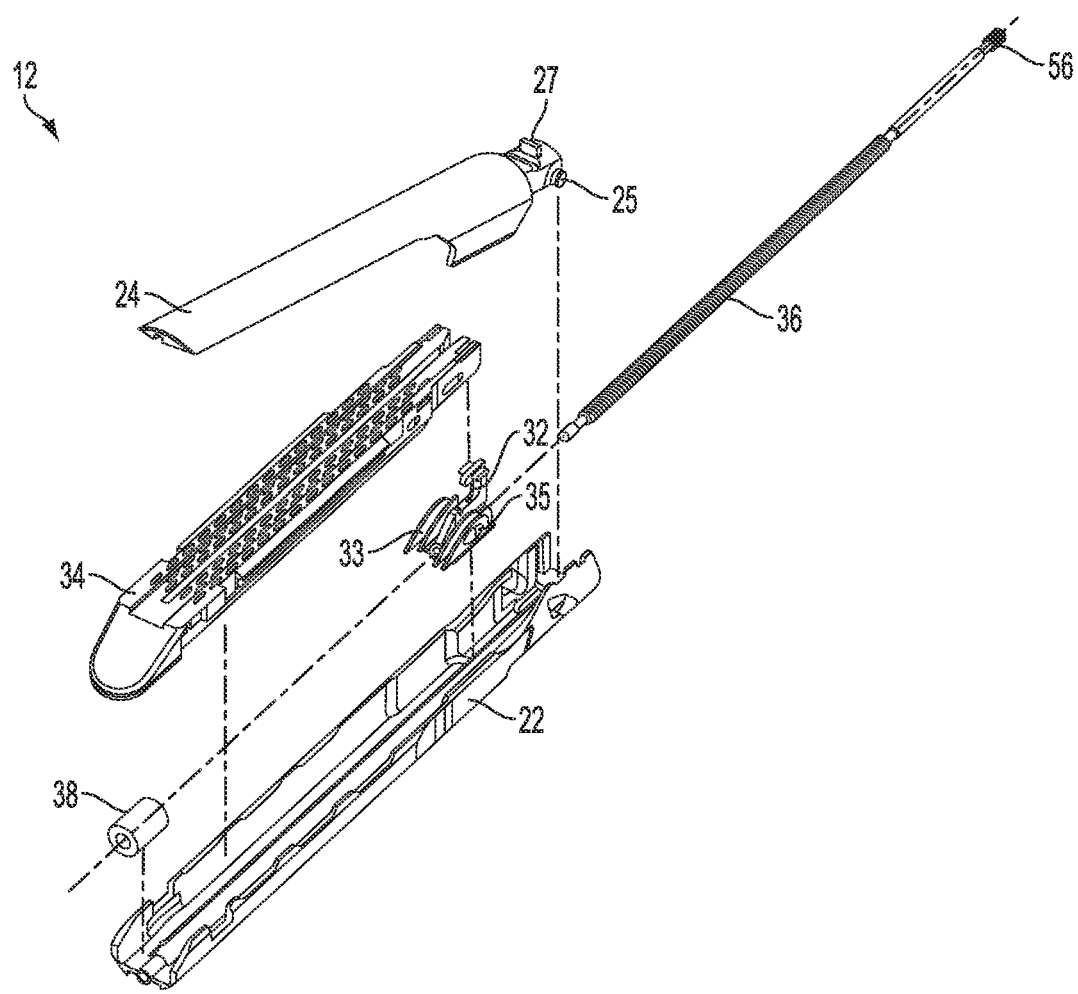
FIGS. 3-5 are exploded views of an end effector and shaft of the instrument according to various embodiments of the present invention.

FIG. 3 is an exploded view of the end effector 12 according to various embodiments. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The second element 35 may be coupled or formed integrally with a component of interest. The cutting instrument 32 may be, for example, a knife. The anvil 24 may be pivotably opened and closed at a pivot point 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot point 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. U.S. Pat. No. 6,978,921, entitled "SURGICAL STAPLING INSTRUMENT INCORPORATING AN E-BEAM FIRING MECHANISM," which is incorporated herein by reference, provides more details about such two-stroke cutting and fastening instruments. The sled 33, which may comprise the second element 35, may be part of the cartridge 34, such that when the knife 32 retracts following the cutting operation, the sled 33 and the second element 35 do not retract. The cartridge 34 could be made of a nonconductive material (such as plastic). In one embodiment, the second element 35 may be connected to or disposed in the cartridge 34, for example. In the illustrated embodiment, the second element 35 may be attached to the sled 33 in any suitable manner and on any suitable portion thereof. In other embodiments, the second element 35 may be embedded in the sled 33 or otherwise integrally formed (e.g., co-molded) with the sled 33. Accordingly, the location of the sled 33 may be determined by detecting the location of the second element 35. The second element 35 may be formed of various materials in various sizes and shapes and may be located at certain predetermined distances from the first element 21 to enable the control unit 300 to ascertain the type, presence and status of the staple cartridge 34.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled "ELECTROSURGICAL HEMOSTATIC DEVICE" to Yates et al., and U.S. Pat. No. 5,688,270, entitled "ELECTROSURGICAL HEMOSTATIC DEVICE WITH RECESSED AND/OR OFFSET ELECTRODES" to Yates et al., which are incorporated herein by reference, discloses cutting instruments that use RF energy to fasten the severed tissue. U.S. patent application Ser. No. 11/267,811 to Morgan et al. and U.S. patent application Ser. No. 11/267,363 to Shelton et al., which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

Figure 4:
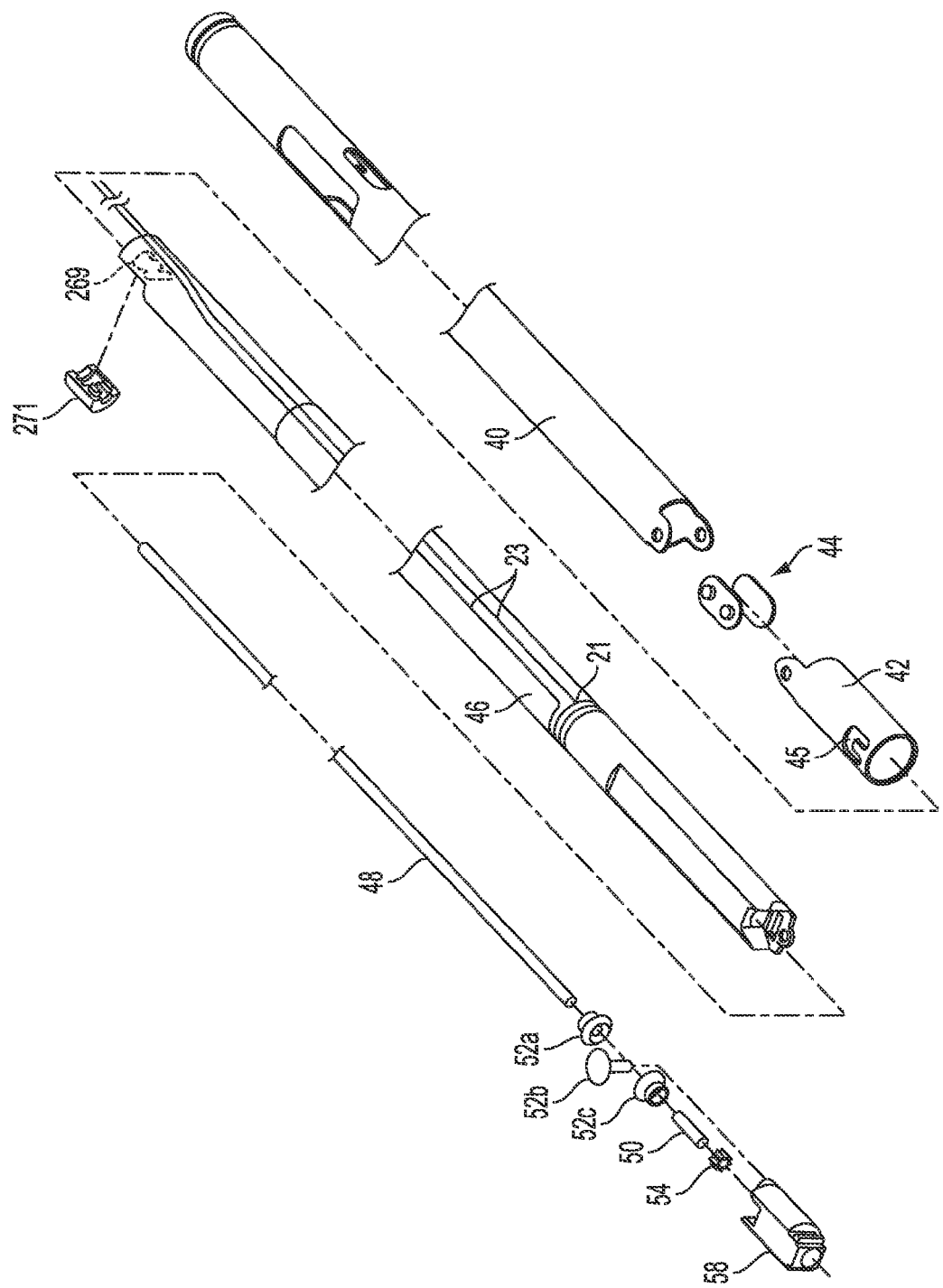
Figure 5:
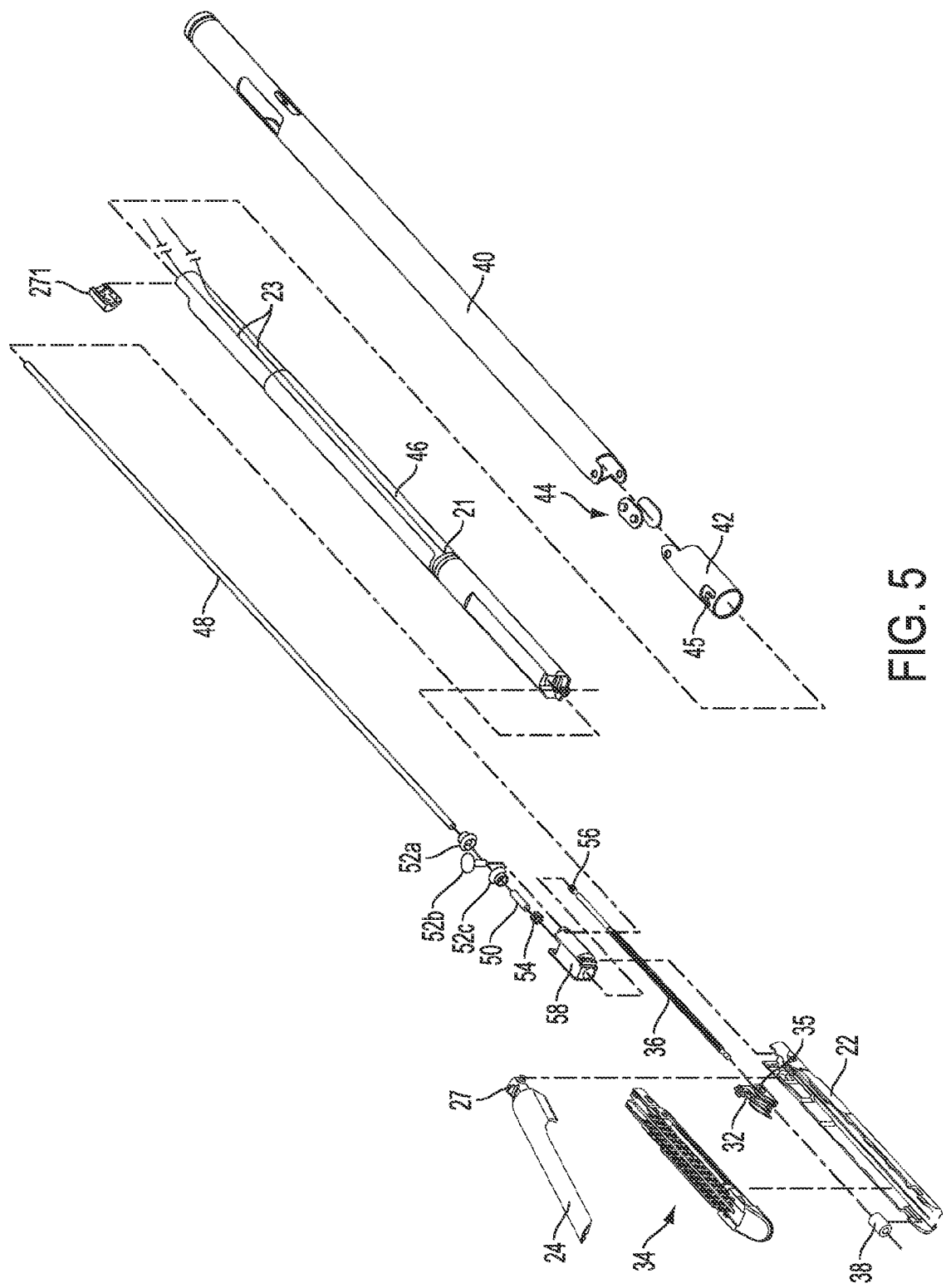
Figure 6:
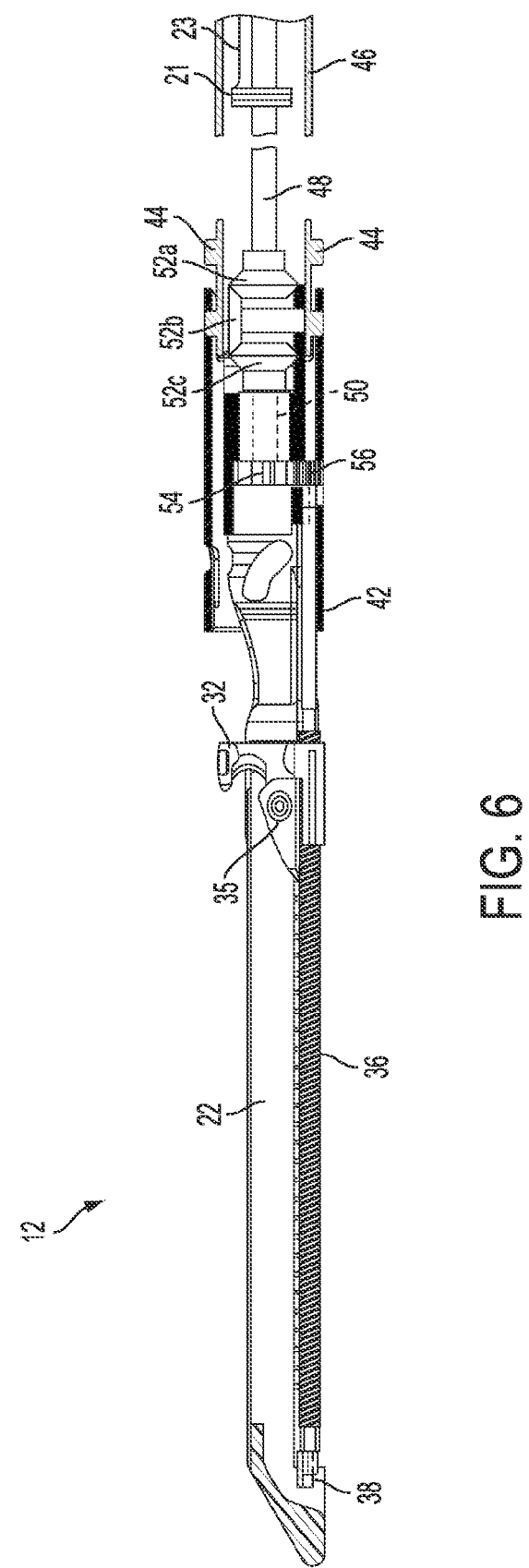
FIG. 6 is a side view of the end effector according to various embodiments of the present invention.
Figure 7:
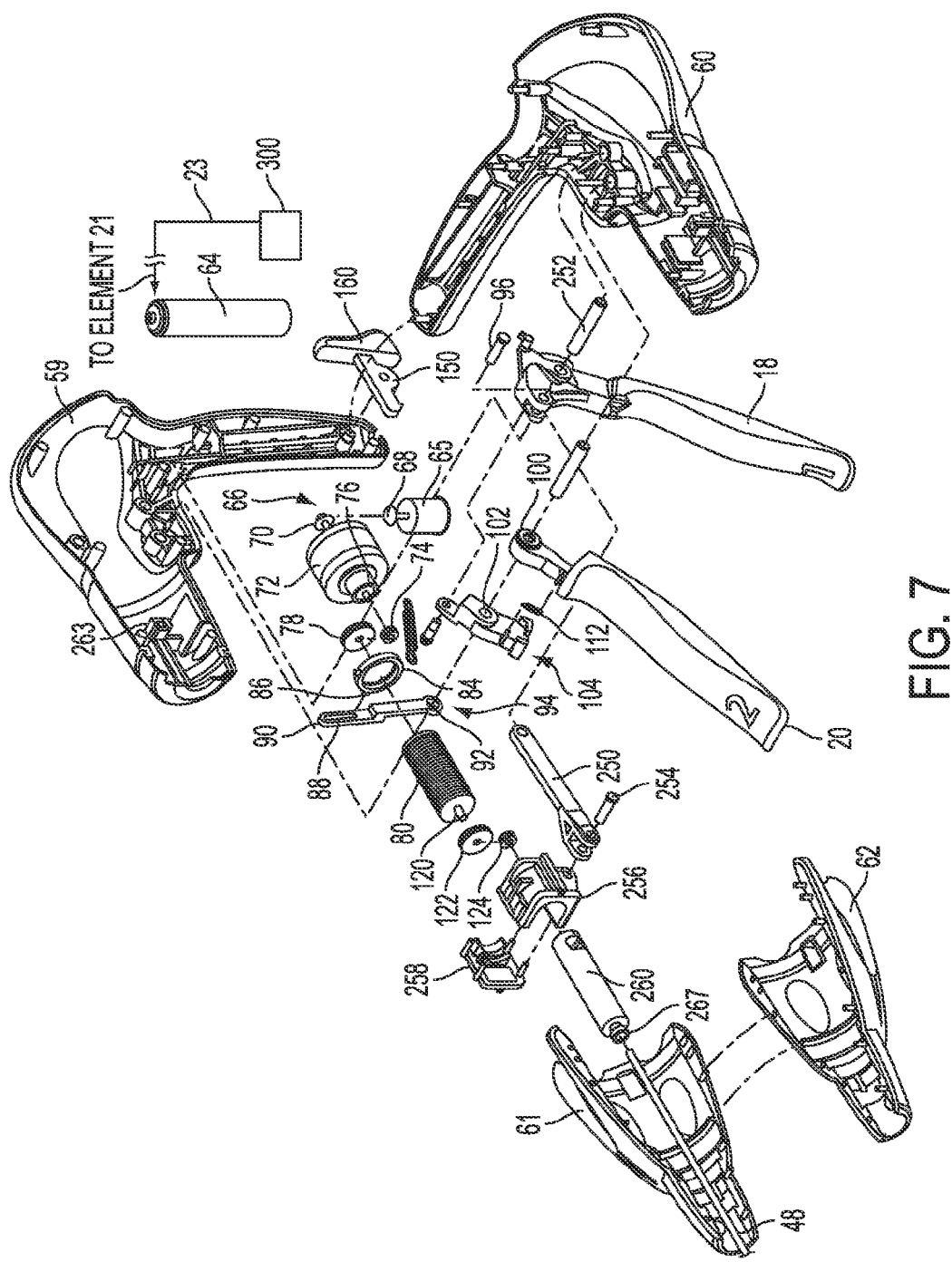
FIG. 7 is an exploded view of the handle of the instrument according to various embodiments of the present invention.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. In the illustrated embodiment, the first element 21 may be a coil disposed about the proximate spine tube 46 (e.g., as shown in FIGS. 4 and 5). In a wired electrical connection configuration, the first element 21 may be connected to the control unit 300 by way of the wired electrical connection 23, which may comprise lengths of wire forming the coil. The lengths of wire may be provided along the proximate spine tube 46 to connect to the control unit 300. In a wireless electrical connection configuration, a wire is not necessary and the electrical connection 23 to the control unit 300 is a wireless electrical connection. In one embodiment, the first element 21 may be contained within the proximate spine tube 46 (e.g., as shown in FIG. 6). In either case, the first element 21 is electrically isolated from the proximate spine tube 46.

The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c), are sometimes referred to herein as the "main drive shaft assembly." Components of the main drive shaft assembly (e.g., the drive shafts 48, 50) may be made of a nonconductive material (such as plastic).

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52*a*-*c* causes the secondary drive shaft 50 to rotate, which in turn, because of the engagement of the drive gears 54, 56, causes the helical screw shaft 36 to rotate, which causes the knife 32 to travel longitudinally along the channel 22 to cut any tissue clamped within the end effector. The sled 33 may be made of, for example, plastic, and may have a sloped distal surface. As previously discussed, the second element 35 may be attached to the sled 33 in any suitable manner to determine the status, location and type of the sled 33 and/or the staple cartridge 34. As the sled 33 traverses the channel 22, the sloped forward surface may push up or drive the staples in the staple cartridge 34 through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

According to various embodiments, as shown FIGS. 7-10, the surgical instrument may include a battery 64 in the handle 6. The illustrated embodiment provides user-feedback regarding the deployment and loading force of the cutting instrument in the end effector 12. In addition, the embodiment may use power provided by the user in retracting the firing trigger 18 to power the instrument 10 (a so-called "power assist" mode). As shown in the illustrated embodiment, the handle 6 includes exterior lower side pieces 59, 60 and exterior upper side pieces 61, 62 that fit together to form, in general, the exterior of the handle 6. The handle pieces 59-62 may be made of an electrically nonconductive material, such as plastic. A battery 64 may be provided in the pistol grip portion 26 of the handle 6. The battery 64 powers a motor 65 disposed in an upper portion of the pistol grip portion 26 of the handle 6. The battery 64 may be constructed according to any suitable construction or chemistry including, for example, a Li-ion chemistry such as $LiCoO_2$ or $LiNiO_2$, a Nickel Metal Hydride chemistry, etc. According to various embodiments, the motor 65 may be a DC brushed driving motor having a maximum rotation of, approximately, 5000 to 100,000 RPM. The motor 64 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 100, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 at its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the control unit which sends a signal to the motor 65 to reverse its rotation direction, thereby withdrawing the knife 32 of the end effector 12 following the cutting operation.

The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

The handle 6 also may comprise the control unit 300. The control unit 300 may be powered through the battery 64 with the addition of a conditioning circuit (not shown). The control unit 300 is coupled to the first element 21 by an electrical connection 23. As previously discussed, the electrical connection 23 may be a wired electrical connection or a wireless electrical connection.

In operation, when an operator of the instrument 10 pulls back the firing trigger 20, the sensor 110 detects the deployment of the firing trigger 20 and sends a signal to the control unit which sends a signal to the motor 65 to cause forward rotation of the motor 65 at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and the sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the control unit which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
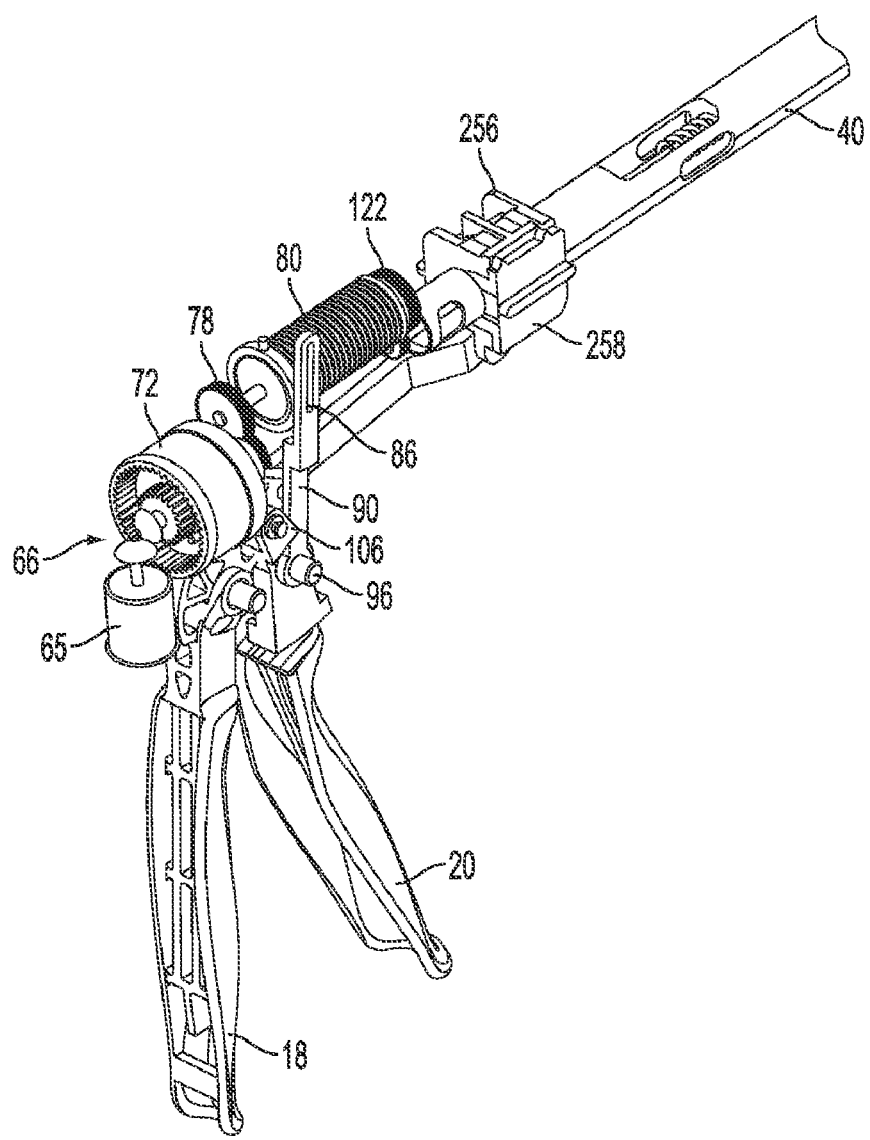
FIGS. 8 and 9 are partial perspective views of the handle according to various embodiments of the present invention.
Figure 9:
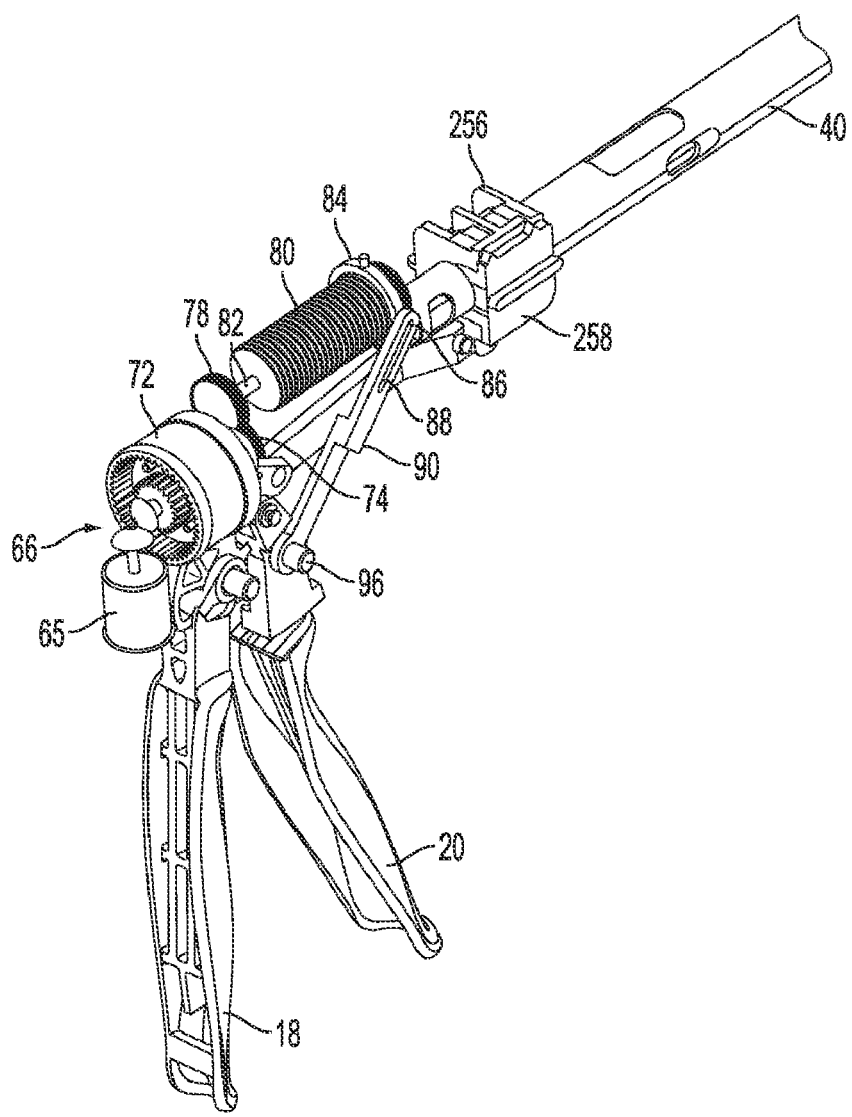
Figure 10:
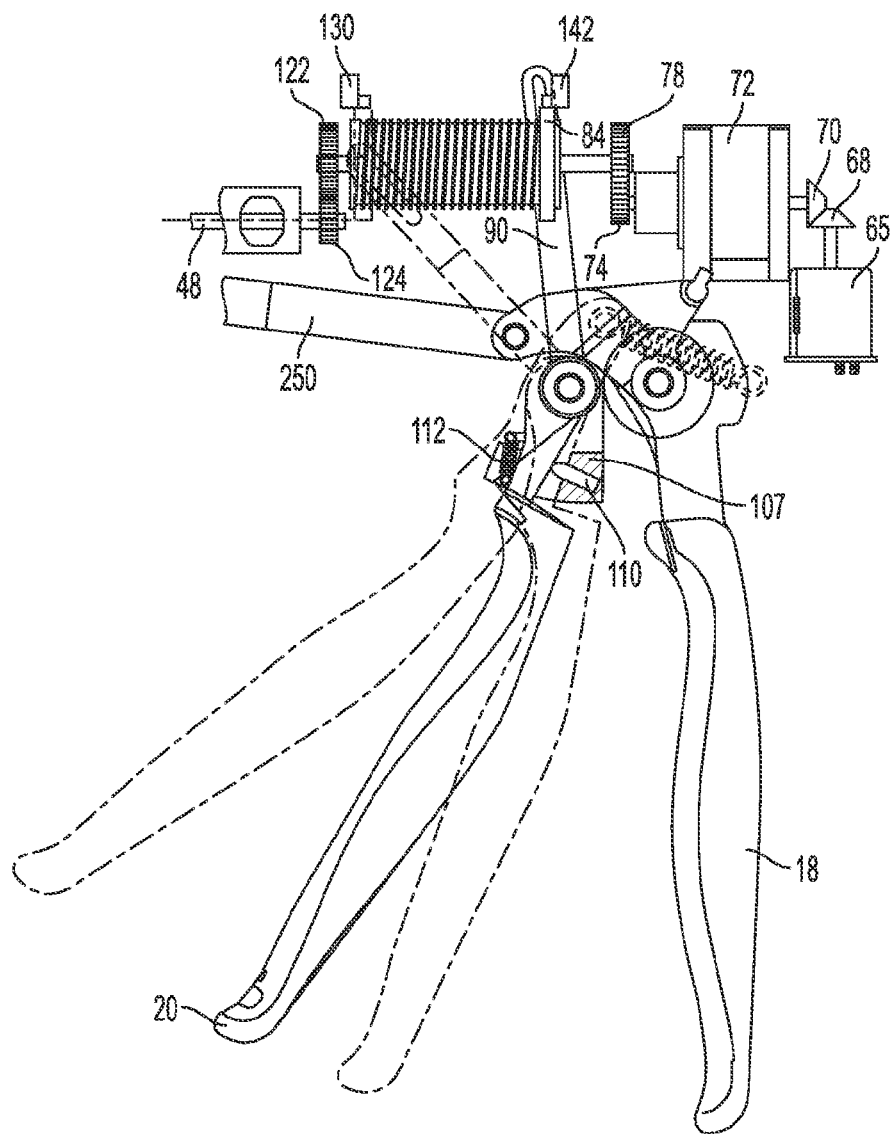
FIG. 10 is a side view of the handle according to various embodiments of the present invention.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 18 from the locked position.

The control unit 300 (described further below) may receive the outputs from end-of-stroke and beginning-of-stroke sensors 130, 142 and the run-motor sensor 110, and may control the motor 65 based on the inputs. For example, when an operator initially pulls the firing trigger 20 after locking the closure trigger 18, the run-motor sensor 110 is actuated. If the staple cartridge 34 is present in the end effector 12, a cartridge lockout sensor (not shown) may be closed, in which case the control unit may output a control signal to the motor 65 to cause the motor 65 to rotate in the forward direction. When the end effector 12 reaches the end of its stroke, the reverse motor sensor 130 will be activated. The control unit may receive this output from the reverse motor sensor 130 and cause the motor 65 to reverse its rotational direction. When the knife 32 is fully retracted, the stop motor sensor switch 142 is activated, causing the control unit to stop the motor 65.

In other embodiments, rather than a proportional-type sensor 110, an on-off type sensor may be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

The instrument 10 may include a number of sensor elements in the end effector 12 for sensing various conditions related to the end effector 12, such as sensor elements for determining the status of the staple cartridge 34 (or other type of cartridge depending on the type of surgical instrument), the progress of the stapler during closure and firing, etc. The sensor elements may be passively powered by inductively coupled signals, as described in commonly assigned U.S. patent application Ser. No. 11/651,715, titled "SURGICAL INSTRUMENT WITH WIRELESS COMMUNICATION BETWEEN CONTROL UNIT AND SENSOR TRANSPONDERS," by J, Giordano et al., which is incorporated herein by reference. In other embodiments, the sensor elements reflect or scatter incident electromagnetic energy or power up in response to the interrogation signal and transmit echo response pulses or signals that may be coupled back to the control unit 300 for processing. In other embodiments, the sensor elements may be powered by the minute electrical current induced in the sensor element itself or an antenna coupled to the sensor element by the incoming incident electromagnetic energy (e.g., the RF carrier of the interrogation signal) transmitted by the control unit 300. These sensor elements may comprise any arrangement of electrical conductors to transmit, receive, amplify, encode, scatter and/or reflect electromagnetic energy waves of any suitable predetermined frequency (e.g., wavelength [λ]), having a suitable predetermined pulse width that may be transmitted over a suitable predetermined time period. The passive sensor elements may comprise any suitable arrangement of resistive, inductive, and/or capacitive elements. The active sensor elements may comprise semiconductors such as transistors, integrated circuits, processors, amplifiers and/or any combination of these active elements. For succinctness the passive and/or active sensor elements are referred to hereinafter as the first element 21 and the second element 35. The first element 21 may be in wired or wireless communication with the control unit 300, which, as previously discussed, may be housed in the handle 6 of the instrument 10, for example, as shown below in FIG. 11. The first element 21 is in wireless communication with the second element 35.

Figure 11:
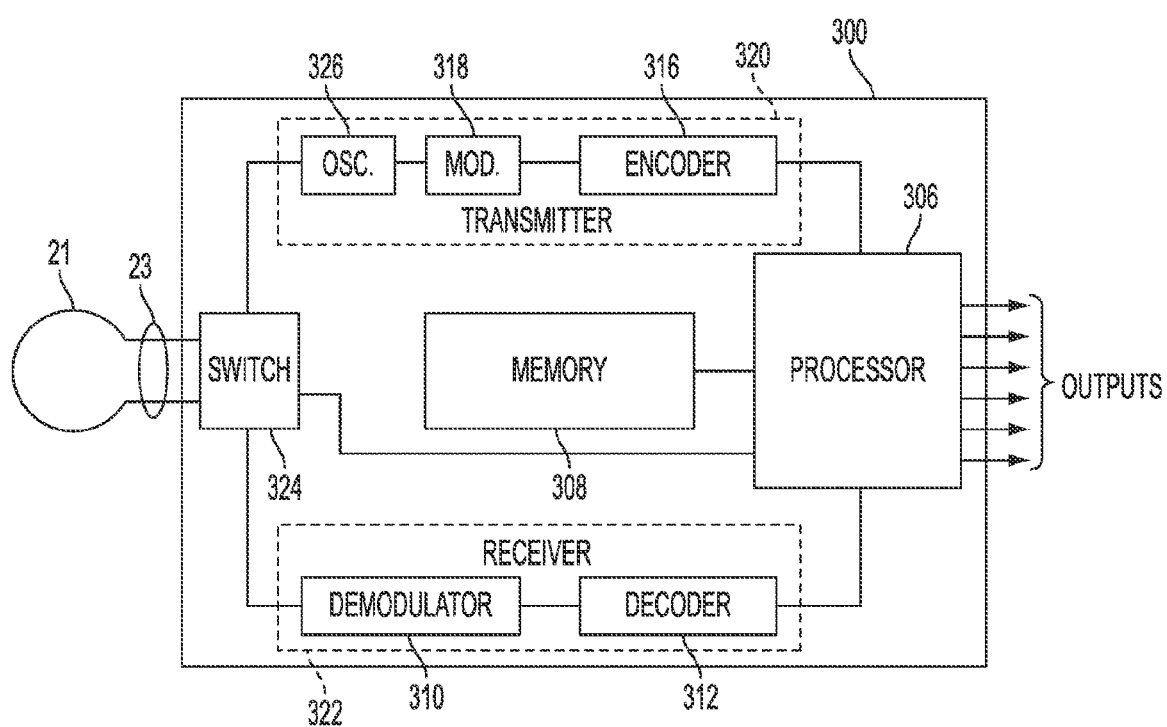
FIG. 11 is a schematic block diagram of one embodiment of a control unit for a surgical instrument according to various embodiments of the present invention.

FIG. 11 illustrates a schematic block diagram of one embodiment of the control unit 300. According to various embodiments, the control unit 300 may comprise a processor 306 and one or more memory units 308. By executing instruction code stored in the memory 308, the processor 306 may control various components of the instrument 10, such as the motor 65 or a user display (not shown), based on inputs received from the one or more end effector sensor element(s) and/or other sensor elements located throughout the instrument 10 (such as the run-motor sensor 110, the end-of-stroke sensor 130, and the beginning-of-stroke sensor 142, for example). The control unit 300 may be powered by the battery 64 during surgical use of the instrument 10. The control unit 300 may be coupled to the first element 21 over the electrical connection 23 and may communicate with the second element 35, as described in more detail below. The control unit 300 may comprise a transmitter 320 and a receiver 322. The first element 21 may be coupled to the transmitter 320 to transmit an output interrogation signal or may be coupled to the receiver 322 to receive an echo response signal in accordance with the operation of a switch 324.

The switch 324 may operate under the control of the processor 306, the transmitter 320 or the receiver 322 or any combination thereof to place the control unit 300 either in transmitter or receiver mode. In transmitter mode, the switch 324 couples the first element 21 to the transmitter 320 and thus the first element 21 acts as a transmitting antenna. An encoder 316 encodes the output interrogation signal to be transmitted, which is then modulated by a modulator 318. An oscillator 326 coupled to the modulator 318 sets the operating frequency for the output signal to be transmitted. In receiver mode, the switch 324 couples the first element 21 to the receiver 322. Accordingly, the first element 21 acts as a receiving antenna and receives input signals from the other sensor elements (e.g., the second element 35). The received input signals may be demodulated by a demodulator 310 and decoded by a decoder 312. The input signals may comprise echo response signals from one or more of the sensor elements (e.g., the second element 35). The echo response signals may comprise information associated with the location, type, presence and/or status of various components located in the end effector 12 or in other location in the instrument 10. The echo signals, for example, may comprise signals reflected by the second element 35, which may be attached to the sled 33, the staple cartridge 34 or any other component located in the end effector 12 or may be located on any component of interest on any portion of the instrument 10. The echo signal data reflected from the second element 35 may be used by the processor 306 to control various aspects of the instrument 10.

To transmit an output signal from the first element 21 to the second element 35, the control unit 300 may employ the encoder 316 for encoding the output signals and the modulator 318 for modulating the output signals according to a predetermined modulation scheme. As previously discussed, in transmitter mode, the first element 21 is coupled to the transmitter 320 through the switch 324 and acts as a transmitting antenna. The encoder 316 may comprise a timing unit to generate timing pulses at a predetermined suitable pulse repetition frequency. These timing pulses may be applied to the modulator 318 to trigger the transmitter at precise and regularly occurring instants of time. Thus, in one embodiment, the modulator 318 may produce rectangular pulses of known pulse duration to switch the oscillator 326 on and off. In accordance with the modulation scheme, the oscillator 326 produces short duration pulses of a predetermined power and frequency (or wavelength λ) set by the oscillator 326. The pulse repetition frequency may be determined by the encoder 312 and the pulse duration may be determined by the modulator 318. The switch 324 under control of the control unit 300 automatically connects the transmitter 320 to the first element 21 for the duration of each output pulse. In transmission mode, the first element 21 radiates the transmitter 320 output pulse signal and picks up or detects the reflected echo signals for application to the receiver 322. In receiver mode, the switch 324 connects the first element 21 to the receiver 322 for the intervals between transmission pulses. The receiver 322 receives echo signals of the transmitted pulse output signals that may be reflected from one or more sensor elements located on the instrument such as the second element 35 attached to the sled 33. The receiver 322 amplifies the echo signals and presents them to the demodulator 310 in suitable form. Subsequently, the demodulated echo signals are provided to the decoder 312 where they are correlated with the transmitted output pulse signals to determine the location, type, presence and/or status of various components located in the end effector 12. In addition, the distance between the first and second elements 21, 35 may be determined.

The control unit 300 may communicate with the first element 21 using any suitable wired or wireless communication protocol and any suitable frequency (e.g., an ISM band). The control unit 300 may transmit output pulse signals in various frequency ranges. Although in the illustrated embodiment, only the first element 21 is shown to perform the transmission and reception functions, in other embodiments the control unit 300 may comprise separate receiving and transmitting elements, for example.

According to various embodiments, the control unit 300 may be implemented using integrated and/or discrete hardware elements, software elements, or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontroller, system-on-chip (SoC) or system-in-package (SIP). Examples of discrete hardware elements may include circuits, circuit elements (e.g., logic gates, field effect transistors, bipolar transistors, resistors, capacitors, inductors, relay and so forth). In other embodiments, the control unit 300 may be embodied as a hybrid circuit comprising discrete and integrated circuit elements or components on one or more substrates. In various embodiments, the control unit 300 may provide a digital (e.g., on/off, high/low) output and/or an analog output to a motor control unit. The motor control unit also may be embodied using elements and/or components similar to the control unit 300. The motor control unit may be used to control the motor 65 in response to the radiated echo response signals from the one or more passive and/or active sensor elements.

Referring back to FIGS. 1-6, in one embodiment, the first element 21 may be an inductive element (e.g., a first coil) coupled to the control unit 300 by the wired electrical connection 23. The wired electrical connection 23 may be an electrically conductive insulated wire. The second element 35 also may be an inductive element (e.g., a second coil) embedded, integrally formed with or otherwise attached to the sled 33. The second element 35 is wirelessly coupled to the first element 21. The first element 21 is preferably electrically insulated from the conductive shaft 8. The second element 35 is preferably electrically insulated from the sled 33 and other components located in the staple cartridge 34 and/or the staple channel 22. The second element 35 receives the output pulse signal transmitted by the first element 21 and reflects or scatters the electromagnetic energy in the form of an echo signal. By varying the material, size, shape and location of the second element 35 relative to the first element 21, the control unit 300 can determine the location, type, presence and/or status of various components located in the end effector 12 by decoding the echo signals reflected therefrom.

Figure 12:
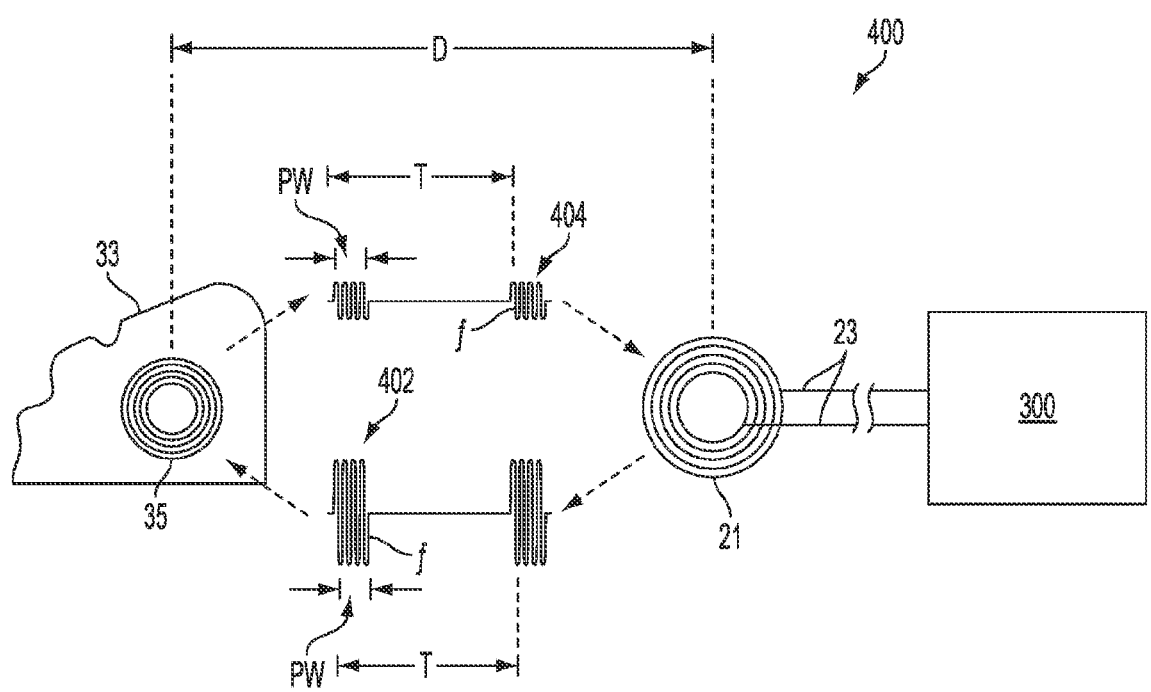
FIG. 12 is a schematic diagram illustrating the operation of one embodiment of the control unit in conjunction with first and second sensor elements for a surgical instrument according to various embodiments of the present invention.

FIG. 12 is a schematic diagram 400 illustrating the operation of one embodiment of the control unit 300 in conjunction with the first and second elements 21, 35. The following description also references FIG. 11. The first element 21 is coupled to the control unit 300 by a channel, e.g., the electrical connection 23. The electrical connection 23 may be a wired or wireless channel. As previously discussed, the first element 21 wirelessly interrogates or illuminates the second element 35 by transmitting an interrogation signal in the form of one or more interrogation pulses 402. The interrogation pulses 402 may be of a suitable predetermined frequency f as may be determined by the oscillator 326. The interrogation pulses 402 may have a predetermined pulse width PW as may be determined by the modulator 318 and may be transmitted at a pulse repetition rate T as may be determined by the encoder 316. The transmitted interrogation pulses 402 that are incident upon (e.g., strike or illuminate) the second element 35 is reflected or scattered by the second element 35 in the form of echo response pulses 404. The echo response pulses 404 are electromagnetic energy reflections of the interrogation pulses 402 incident upon the second element 21, but much weaker in signal strength. After transmitting the interrogation pulses 402, the first element 21 listens for the echo response pulses 404 and couples the echo response pulses 402 to the control unit 300 in a suitable form. The demodulator 310 receives the weak echo response pulses 404 and amplifies and demodulates them. The decoder 312 and the processor 306 process the received echo response pulses 404 to extract information therefrom. The processor 306 (or other logic) may be programmed to ascertain various properties associated with the end effector 12 and components in accordance with the received echo response pulses 404.

The frequency f, PW and T of the echo response pulses 404 may be the same as the interrogation pulses 402. In various embodiments, the frequency f, PW and T of the echo response pulses 404 may be different than the interrogation pulses 402. In one embodiment, the frequency f, for example, of the echo response pulses 404 may be a harmonic frequency of the interrogation pulse 402 frequency. The amount of reflected electromagnetic energy in the echo response pulses 404 depends upon the material, shape and size of the second element 35. The amount of reflected electromagnetic energy in the echo response pulses 404 also depends upon the distance D between the first element 21 and the second element 35.

The material that the second element 35 is formed of may determine the amount of reflected energy. For example, a metal object will reflect more energy than an object of the same size and shape made of wood, plastic, etc. In general, the better the electrical conductive properties of the material the greater is the reflection. The shape of the second element 35 also may determine how the energy is reflected or scattered. For example, if the second element 35 has a flat side facing the first element 21, the second element 35 may reflect more energy back towards the first element 21. A circular object may reflect or scatter the energy in the various directions normal to the surface struck by the incident electromagnetic energy and an object with irregularities will scatter the incident electromagnetic energy more randomly. The size of the second element 21 also may determine the amount of reflected energy. For example, a larger second element 35 will reflect more energy than a smaller second element 35 of the same material and shape and at the same distance D from the first element 21. It will be appreciated that the second element 35 should have a certain minimum size relative to the wavelength (λ) of the radiated electromagnetic energy of the interrogation pulses 402 to produce practical reflected echo response pulses 404. For example, the size of the second element 35 may be equal to or greater than about a quarter of the wavelength (λ/4) of the electromagnetic energy of the interrogation pulses 402. The wavelength λ of the transmitted interrogation pulses 402 is related to the frequency f in accordance with the equation: $\lambda = c/f$; where c is the speed of light and f is the signal frequency. Therefore, to detect small objects the wavelength λ must be small and thus the frequency f must be high. Any suitable predetermined frequency f may be selected to accommodate the size of the second element 35 to be detected. Accordingly, the size of the second element 35 may be selected to be greater than or equal to λ/4 (or c/4f), for example, once the interrogation pulse 402 frequency is determined. As previously discussed, the amount of energy reflected by the second element 35 also depends on the distance D between the first element 21 and the second element 35.

Accordingly, the material, shape and size of the second element 35 and the relative distance D between it and the first element 21 may be selected to generate unique echo response pulses 404 that may be indicative of a desired measurement associated with the second element 35. For example, unique echo response pulses 404 may indicate the location, type, presence and/or status of various components and/or sub-components disposed on the surgical instrument 10. Especially the various components and sub-components disposed in the end effector 12 portion of the surgical instrument 10 subsequent to the articulation pivot 14. The echo response pulses 404 also may be used to determine the distance D between the first element 21 and the second element 35. In this manner, by integrating the second element 35 or attaching it to a components of interest, such as the sled 33, the echo response pulses 404 may be processed by the control unit 300 to extract and provide information associated with the component of interest, such as the location, type, presence and/or status of the sled 33, the staple cartridge 34, and so on. This arrangement may eliminate the need to transmit or provide power over a wired connection to the second element 35 and may be a cost effective solution to providing various sensor elements on the surgical instrument 10.

In one embodiment, where the second element 35 is an active sensor element, as previously discussed, the first element 21 wirelessly interrogates or illuminates the second element 35 by transmitting an interrogation signal in the form of one or more interrogation pulses 402. The electromagnetic energy in the interrogation pulses 402 are coupled by the sensor element 35 and serve to power-up the sensor element 35. Once powered-up, the sensor element 35 transmits the echo response pulses 404 back to the control unit 300.

In one embodiment, the status of the staple cartridge 34 and the location of the sled 33 may be determined by transmitting the interrogation pulse 402 and listening for an echo response pulse 404. As previously discussed, the first and second elements 21, 35 may be passive sensors or electromagnetic elements (which may comprise resistive, inductive and capacitive elements o any combination thereof). In one embodiment, the first element 21 may be an inductance in the form of a primary coil located at the distal end of the shaft 8 (as shown in FIGS. 1, 2, 4-6). The second element 35 may be an inductive element in the form of a secondary coil located in the sled 35 (as shown in FIGS. 3, 5, 6). The first element 21 " pings" or transmits interrogation pulses 402. The echo response pulses 404 reflected by the second element 35 may be indicative of the presence of the sled 33 in the staple channel 22, its distance from the first element 21 or its location longitudinally along the staple channel 22. In this manner, the instrument 10 can determine the presence or status of the staple cartridge 34 or the sled 33 in the end effector 12 or the longitudinal location of the sled 35 along the staple channel 22. This information may be used to determine the loaded status of the staple cartridge 34, for example. Further the second element 35 may be formed of different materials, in different shapes or sizes to produce a unique echo response pulse 404 that is indicative of the instrument 10 type or presence of the staple cartridge 34 within the end effector 12. This eliminates the need to include any powered memory or sensor elements in the end effector 12 to electronically determine the type, presence or status of the staple cartridge 34 in the end effector 12.

In another embodiment, the second element 35 may be attached to the sled 33 and the echo response pulse 404 may be used to determine whether the sled 33 is located in a first position at the proximal end of the staple channel 22 or a second position at the distal end of the staple channel 22 or in any intermediate positions therebetween. The control unit 300 may be determine the position of the sled 33 based on the elapsed time between transmitting the interrogation pulse 402 and receiving the echo response pulse 404. If the sled 33 is in the first position the echo response pulse 404 is received sooner than if the sled 33 was located at the second position or any position therebetween. For example, as the sled 33 moves longitudinally along the staple channel 22 the response time of the received echo response pulse 404 relative to the transmitted interrogation pulse 402 increases. This information may be used by the control unit 300 to determine the intermediate location of the sled 33 in the channel 22 and provide some measure of control of the cutting/fastening operation, such as inhibiting the cutting/fastening operation if the sled 33, or other component, is not in a predetermined location.

In yet another embodiment, the control unit 300 may provide some measure of control of the cutting/fastening operation based on whether or not an echo response pulse 404 is received within a predetermined time period. For example, if an echo response pulse 404 is received within the predetermined period, the control unit 300 determines that the sled 33 in located in the proximate end on the staple channel 22. In contrast, if the no echo response pulse 404 is received within the predetermined period, the control unit 300 determines that the sled 33 has moved away from the proximate end to the distal end of the staple channel 22 (e.g., the instrument has been fired). In this manner, if no echo response pulse 404 is received, the control unit 300 may determine either that the staple cartridge 34 has been fired and, therefore, the sled 33 has moved away longitudinally from the proximate end of the staple channel 22 or that there is no staple cartridge 34 loaded and, therefore, prevents the instrument 10 (e.g., a surgical stapler) from firing.

Although the first element 21 is shown disposed at one end of the elongate shaft 8 near the articulation pivot 14, the first element 21 may be disposed anywhere along the elongate shaft 8 and/or in the handle 6 in suitable wireless or wired communication with the second element 35.

Figure 13:
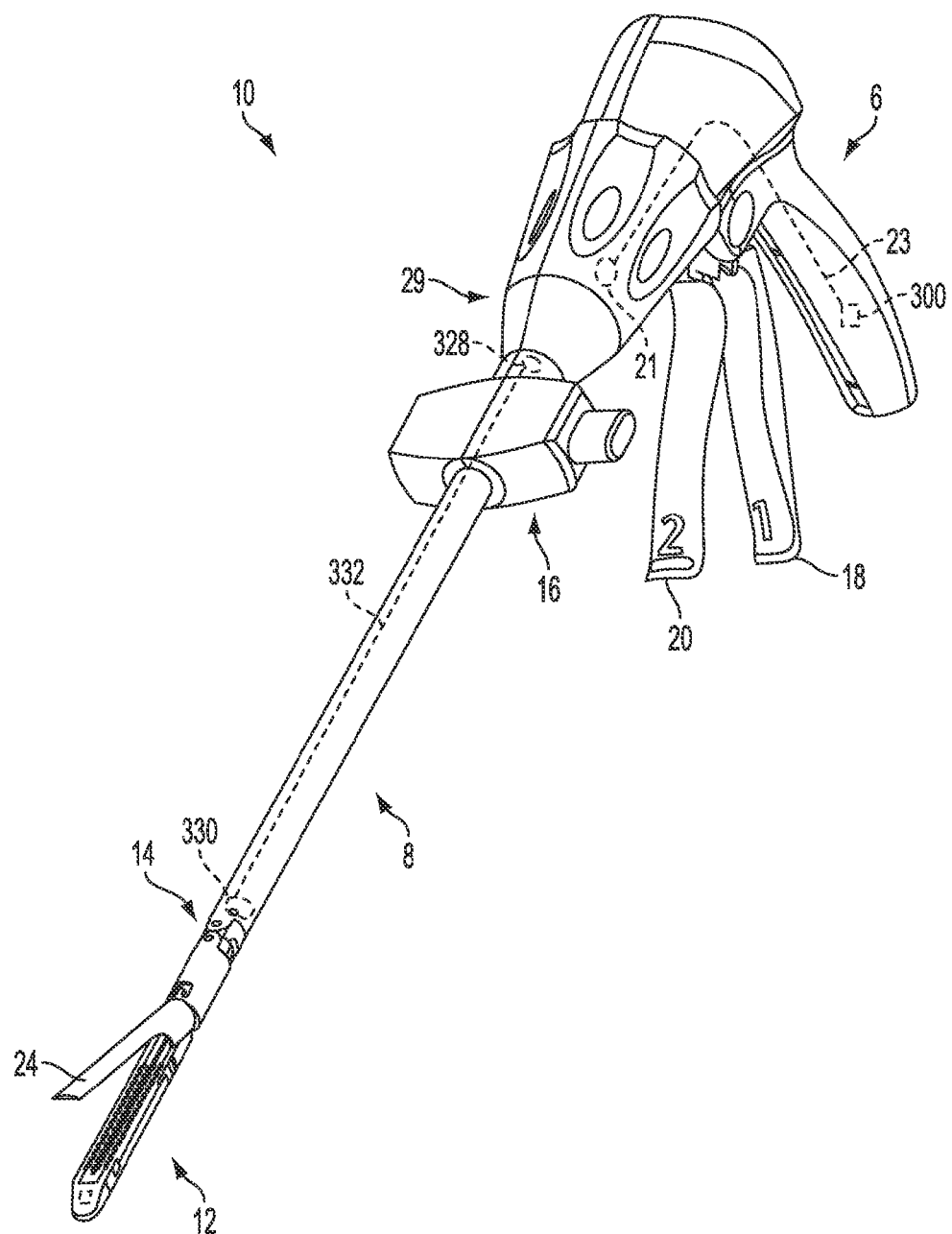
FIG. 13 illustrates one embodiment of a surgical instrument comprising a first element located in a free rotating joint portion of a shaft of the surgical instrument.

FIG. 13 illustrates one embodiment of the surgical instrument 10 comprising the first element 21 located in the free rotating joint 29 portion of the shaft 8. The following description also references FIGS. 3, 5, 6 and 12. The first element 21 is coupled to the control unit 300 via the electrical connection 23. Additional elements may be employed, for example, when the surgical instrument 10 has numerous complex mechanical joints and where it would be difficult to maintain a direct wired connection. In such cases, inductive couplings may be used to span each such joint. For example, inductive couplers may be used on both sides of the rotary joint 29 and both sides of the articulation pivot 14, with an inductive element on the distal side of the rotary joint 29 connected by an electrical connection to another inductive element on the proximate side of the articulation pivot 14. Accordingly, a third element 328 and a fourth element 330 may be disposed on the shaft 8. These elements 328, 330 may disposed anywhere along the shaft 8. The third element 328 may be disposed on the proximal end of the shaft 8 just prior to the articulation control 16. The fourth element 330 may be disposed on the distal end of the shaft 8 just prior to the articulation pivot 14. The third and fourth elements 328, 330 may be coupled by an electrical connection 332, which may be a wired or a wireless electrical connection. The second element 35 is disposed or attached to a component of interest in the end effector 12. The third element 328 is wirelessly coupled to the first element 21 and receives interrogation pulses 402 therefrom. The third element 328 transmits the interrogation pulse 402 along the electrical connection 332 to the fourth element 330. The fourth element 330 wirelessly couples the interrogation pulse 402 to the second element 35. The echo response pulses 404 are transmitted back to the first element 21 in reverse order. For example, the echo response pulse 404 is wirelessly coupled to the fourth element 330, is relayed to the third element 328 via the electrical connection 332 and is then wirelessly coupled to the first element 21. Similarly to the first and second elements 21, 35, the third and fourth elements 328, 330 may be formed of passive and/or active sensor elements (e.g., resistive, inductance, capacitive and/or semiconductor elements). In one embodiment, the third and fourth elements 328, 330 may be passive coils formed of various materials and in various shapes and sizes or may comprise semiconductor elements such as transistors to operate in active mode.

Figure 14:
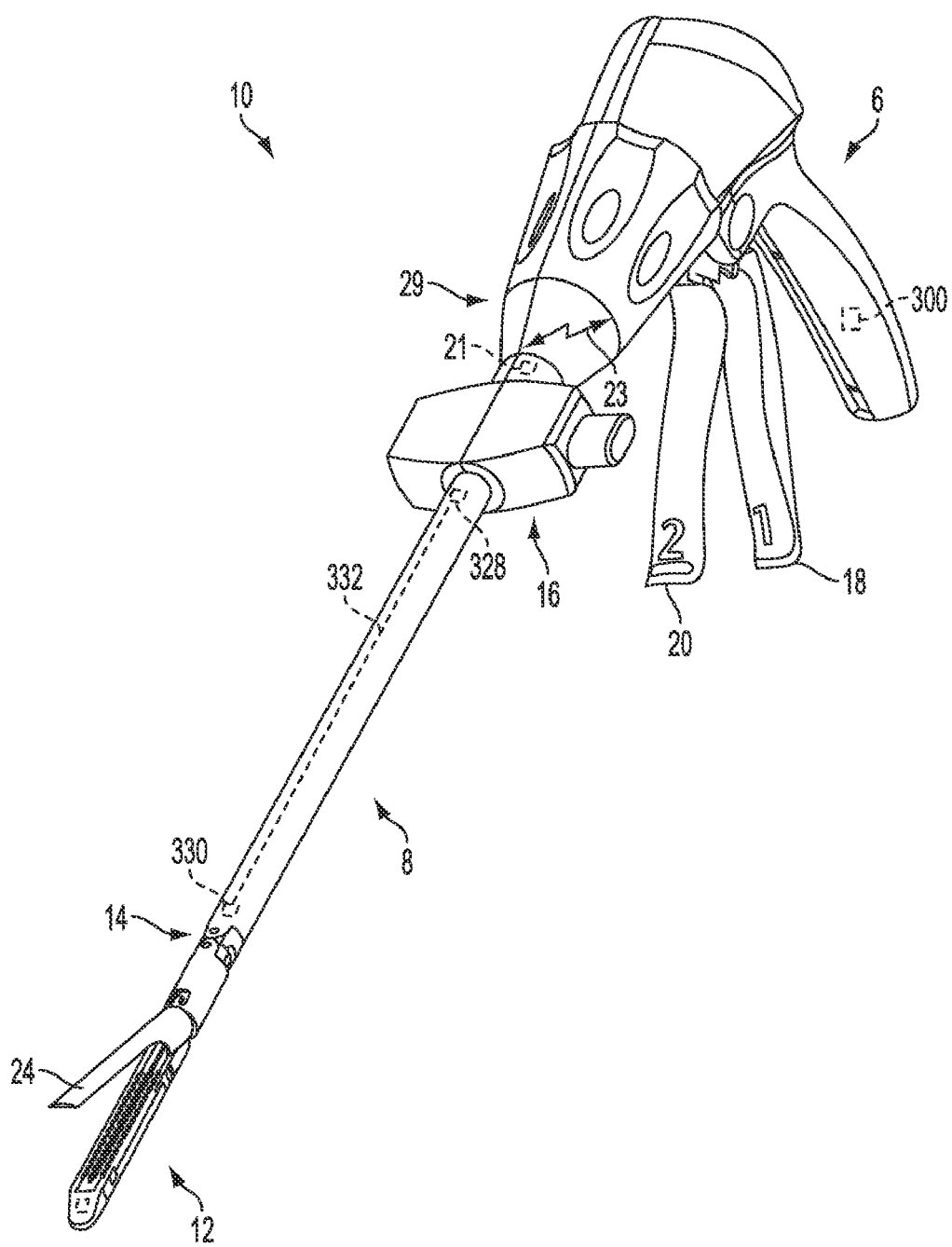
FIG. 14 illustrates one embodiment of a surgical instrument comprising sensor elements disposed at various locations on a shaft of the surgical instrument.

FIG. 14 illustrates one embodiment of the surgical instrument 10 comprising sensor elements disposed at various locations on the shaft. For example, the first element 21 may be disposed on the proximate end of the shaft 8 just prior to the articulation control 16. The first element 21 is wirelessly coupled to the control unit 300 via wireless electrical connection 23. The third element 328 and the fourth element 330 are disposed along the shaft 8 subsequent to the articulation control 16 and prior to the articulation pivot 14. The third element 328 may be disposed on the proximate end of the shaft 8 subsequent to the articulation control 16 and the fourth element 330 may be disposed on the distal end of the elongate shaft 8 prior to the articulation pivot 14. The third and fourth elements 328, 330 are coupled by the electrical connection 332, which may be a wired or a wireless electrical connection. As previously discussed, the second element 35 may be disposed on a component of interest located in the end effector 12. The third element 328 is wirelessly coupled to the first element 21 and receives the interrogation pulses 402 therefrom. The third element 328 transmits the interrogation pulse 402 along the electrical connection 332 to the fourth element 330. The fourth element 330 wirelessly couples the interrogation pulse 402 to the second element 35. The echo response pulses 404 are transmitted back to the first element 21 in reverse order. For example, the echo response pulse 404 is wirelessly coupled to the fourth element 330, is relayed to the third element 328 via the electrical connection 332 and is wirelessly coupled to the first element 21 thereafter.

Figure 15:
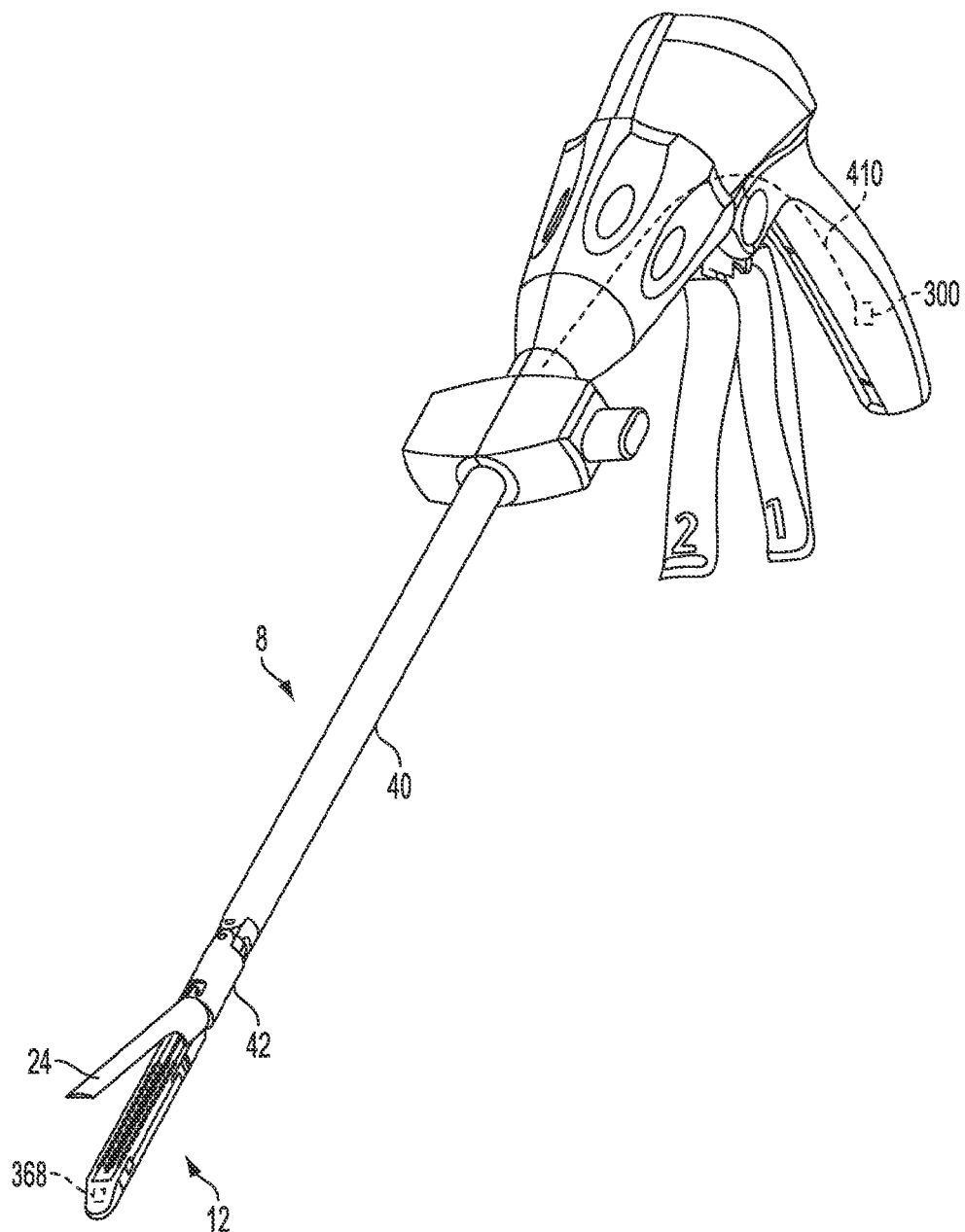
FIG. 15 illustrates one embodiment of a surgical instrument where a shaft of the surgical instrument serves as part of an antenna for a control unit.

FIG. 15 illustrates one embodiment of the instrument 10 where the shaft serves as part of the antenna for the control unit 300. Accordingly, the shaft 8 of the instrument 10, including for example, the proximate closure tube 40 and the distal closure tube 42, may collectively serve as part of an antenna for the control unit 300 by radiating the interrogation pulses 402 to the second element 35 and receiving the echo response pulses 404 reflected from the second element 35. That way, signals to and from the control unit 300 and the second element 35 disposed in the end effector 12 may be transmitted via the shaft 8 of the instrument 10.

The proximate closure tube 40 may be grounded at its proximate end by the exterior lower and upper side pieces 59-62, which may be made of a nonelectrically conductive material, such as plastic. The drive shaft assembly components (including the main drive shaft 48 and secondary drive shaft 50) inside the proximate and distal closure tubes 40, 42 may also be made of a nonelectrically conductive material, such as plastic. Further, components of the end effector 12 (such as the anvil 24 and the channel 22) may be electrically coupled to (or in direct or indirect electrical contact with) the distal closure tube 42 such that they may also serve as part of the antenna. Further, the second element 35 may be positioned such that it is electrically insulated from the components of the shaft 8 and the end effector 12 serving as the antenna. For example, the second element 35 may be positioned in the cartridge 34, which may be made of a nonelectrically conductive material, such as plastic. Because the distal end of the shaft 8 (such as the distal end of the distal closure tube 42) and the portions of the end effector 12 serving as the antenna may be relatively close in distance to the second element 35, the power for the transmitted signals may be held at low levels, thereby minimizing or reducing interference with other systems in the use environment of the instrument 10.

In such an embodiment, the control unit 300 may be electrically coupled to the shaft 8 of the instrument 10, such as to the proximate closure tube 40, by an electrically conductive connection 410 (e.g., a wire). Portions of the outer shaft 8, such as the closure tubes 40, 42, may therefore act as part of an antenna for the control unit 300 by radiating signals in the form of interrogation pulses 402 to the second element 35 and receiving radiated signals in the form of echo response pulses 404 from the second element 35. The echo response pulses 404 received by the control unit 300 may be demodulated by the demodulator 310 and decoded by the decoder 312 as previously discussed. The echo response pulses 404 may comprise information from the second element 35 such as, the location, type, presence and/or status of various components disposed on the end effector 12 portion of the instrument 10, which the processor 306 may use to control various aspects of the instrument 10, such as the motor 65 or a user display.

To transmit data signals to or from the second element 35 in the end effector 12, the electrical connection 410 may connect the control unit 300 to components of the shaft 8 of the instrument 10, such as the proximate closure tube 40, which may be electrically connected to the distal closure tube 42. The distal closure tube 42 is preferably electrically insulated from the remote sensor 368, which may be positioned in the plastic cartridge 34. As mentioned before, components of the end effector 12, such as the channel 22 and the anvil 24, may be conductive and in electrical contact with the distal closure tube 42 such that they, too, may serve as part of the antenna.

With the shaft 8 acting as the antenna for the control unit 300, the control unit 300 can communicate with the second element 35 in the end effector 12 without a direct wired connection. In addition, because the distances between shaft 8 and the second element 35 is fixed and known, the power levels could be optimized for low levels to thereby minimize interference with other systems in the use environment of the instrument 10.

Although throughout this description, the second element 35 is shown disposed in the articulating end effector 12, the second element 35 may be disposed in any suitable location on the instruments 10 while maintaining wireless communication with the first element 21 (and/or the shaft 8) at least on one portion of the transmission or reception cycle. The second element 35 also may be coupled to any component within the staple cartridge 34.

The control unit 300 may communicate with any of the first 21, second 35, third 328 and fourth 330 elements and additional elements through complex mechanical joints like the rotating joint 29 without a direct wired connection, but rather through a wireless connection where it may be difficult to maintain a wired connection. In addition, because the distances between the first, second, third, fourth 21, 35, 328, 330 elements, and any additional elements and/or any combination thereof, may be fixed and known the couplings between these elements 21, 35, 328, 330 may be optimized for efficient inductive transfer of electromagnetic energy. Also, these distances may be relatively short so that relatively low power signals may be used and minimize interference with other systems in the use environment of the instrument 10.

In other embodiments, more or fewer sensor elements may be inductively, electromagnetically and/or otherwise coupled. For example, in some embodiments, the control unit 300 may comprise the first element 21 formed integrally therewith. The first element 21 in the handle 6 and the second element 35 in the end effector 12 can communicate directly without the third and fourth elements 328, 330. Of course, in such an embodiment, a stronger signal may be required due to the greater distance between the control unit 300 in the handle 6 and the second element 35 in the end effector 12.

In the embodiments described above, the battery 64 (FIG. 7) powers (at least partially) the firing operation of the instrument 10. As such, the instrument 10 may be a so-called "power-assist" device. More details and additional embodiments of power-assist devices are described in the '573 application, which is incorporated herein by reference. It should be recognized, however, that the instrument 10 need not be a power-assist device and that this is merely an example of a type of device that may utilize aspects of the present invention. For example, the instrument 10 may include a user display (such as a LCD or LED display) that is powered by the battery 64 and controlled by the control unit 300. Data from the sensor transponders 368 in the end effector 12 may be displayed on such a display.

The various embodiments of the present invention have been described above in connection with cutting-type surgical instruments. It should be noted, however, that in other embodiments, the inventive surgical instrument disclosed herein need not be a cutting-type surgical instrument, but rather could be used in any type of surgical instrument including remote sensor transponders. For example, it could be a non-cutting endoscopic instrument, a grasper, a stapler, a clip applier, an access device, a drug/gene therapy delivery device, an energy device using ultrasound, RF, laser, etc. In addition, the present invention may be in laparoscopic instruments, for example. The present invention also has application in conventional endoscopic and open surgical instrumentation as well as robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument comprising:
   a shaft having a proximal end and a distal end, the shaft comprising a first sensor element to wirelessly transmit an interrogation signal to a second sensor element and receive a wireless echo signal from the second sensor element in response to the wireless interrogation signal;
   an end effector coupled to the distal end of the shaft, the end effector comprising an articulating joint and the second sensor element located across the articulating joint relative to the first sensor element, wherein the second sensor element is not wiredly connected to an electrical power source and is configured to collect electrical power from the incoming wireless interrogation signal transmitted by the first sensor element, the second sensor element configured to generate a unique wireless echo signal for receipt by the first sensor element in response to the wireless interrogation signal transmitted by the first sensor element, wherein the unique wireless echo signal is indicative of a desired measurement associated with the second sensor element; and
   a handle connected to the proximal end of the shaft, the handle comprising a control unit configured to communicate with the first sensor element and the first sensor element is configured for wireless communication with the second sensor element, wherein the control unit is configured to process the unique echo signal transmitted by the second sensor element and received by the first sensor element to extract and provide information associated with the desired measurement associated with the second sensor element.

2. The surgical instrument of claim 1, wherein the handle further comprises:
   a motor in communication with the control unit, wherein the motor is to power a main drive shaft assembly in the shaft, wherein the main drive shaft assembly is to drive the end effector; and
   a battery to supply power to the motor.

3. The surgical instrument of claim 2, wherein the handle further comprises:
   a closure trigger to cause the end effector to clamp an object positioned in the end effector, when retracted by an operator; and
   a firing trigger, separate from the closure trigger, to cause actuation of the motor, when retracted by the operator.

4. The surgical instrument of claim 1, wherein the control unit comprises:
   a transmitter;
   a receiver; and
   a switch coupled to the transmitter, the receiver and the first sensor element;

wherein the switch couples the first sensor element to the transmitter to transmit the interrogation signal to the second sensor element; and wherein the switch couples the first sensor element to the receiver to receive an echo response signal reflected by the second sensor element in response to the interrogation signal.

5. The surgical instrument of claim 4, wherein the control unit comprises:

a processor coupled to the receiver, the processor to determine a status of the end effector based on the echo response signal.

6. The surgical instrument of claim 1, wherein the control unit is in wireless communication with the first sensor element.

7. The surgical instrument of claim 1, wherein the surgical instrument comprises at least one rotational joint for rotating the shaft, wherein the surgical instrument further comprises:

a third sensor element located in the shaft proximally to the rotational joint and in wireless communication with the first sensor element; and a fourth sensor element in communication with the third sensor element, the fourth sensor element is located in the shaft distally from the rotating joint and in wireless communication with the second sensor element.

8. The surgical instrument of claim 7, wherein the at least one rotational joint is located between the third sensor element and the fourth sensor element.

9. The surgical instrument of claim 1, wherein the shaft comprises an articulation pivot between the first and second sensor elements.

10. The surgical instrument of claim 1, wherein the surgical instrument comprises an endoscopic surgical instrument.

11. The surgical instrument of claim 1, wherein the end effector comprises a moveable cutting instrument.

12. The surgical instrument of claim 11, wherein the end effector comprises a staple cartridge.

13. The surgical instrument of claim 1, wherein the desired measurement associated with the second sensor element is any one of a location, type, presence, status of components, and status of subcomponents associated with the surgical instrument.

14. A surgical instrument comprising:

a sensor element not wiredly connected to an electrical power source and configured to collect electrical power from an incoming wireless interrogation signal transmitted by another sensor element, the sensor element configured to generate a unique wireless echo signal for receipt by the other sensor element in response to the wireless interrogation signal transmitted by the other sensor element, wherein the unique wireless echo signal is indicative of a desired measurement associated with the sensor element; and a control unit configured to communicate with the sensor element and to process the unique echo signal transmitted by the sensor element and received by the other sensor element to extract and provide information associated with the desired measurement associated with the sensor element.

15. The surgical instrument of claim 14, further comprising:

a motor in communication with the control unit, wherein the motor is to power a main drive shaft assembly in the shaft, wherein the main drive shaft assembly is to drive the end effector; and a battery to supply power to the motor.

16. The surgical instrument of claim 15, further comprising:

a closure trigger to cause the end effector to clamp an object positioned in the end effector, when retracted by an operator; and a firing trigger, separate from the closure trigger, to cause actuation of the motor, when retracted by the operator.

17. The surgical instrument of claim 14, wherein the control unit comprises:

a transmitter;

a receiver; and a switch coupled to the transmitter, the receiver and the shaft;

wherein the switch couples the shaft to the transmitter to transmit an interrogation signal to the sensor element; and wherein the switch couples the shaft to the receiver to receive an echo response signal reflected by the sensor element in response to the interrogation signal.

18. The surgical instrument of claim 17, wherein the control unit comprises:

a processor coupled to the receiver, the processor to determine a status of the end effector based on the echo response signal.

19. The surgical instrument of claim 14, wherein the surgical instrument comprises an endoscopic surgical instrument.

20. The surgical instrument of claim 14, further comprising a moveable cutting instrument.

21. The surgical instrument of claim 20, further comprising a staple cartridge.

22. The surgical instrument of claim 14, wherein the desired measurement associated with the sensor element is any one of a location, type, presence, status of components, and status of subcomponents associated with the surgical instrument.

* * * * *